(12) United States Patent
Langenfeld et al.

(10) Patent No.: US 10,299,941 B2
(45) Date of Patent: *May 28, 2019

(54) ARM PROSTHETIC DEVICE

(71) Applicant: DEKA Products Limited Partnership, Manchester, NH (US)

(72) Inventors: Christopher C. Langenfeld, Nashua, NH (US); Christopher O. Evans, Amherst, NH (US); Stanley B. Smith, III, Raymond, NH (US); Alexander H. Muller, Manchester, NH (US); John M. Kerwin, Manchester, NH (US); Thomas S. Schnellinger, North Andover, MA (US); G. Michael Guay, Greenville, NH (US); Dirk A. van der Merwe, Manchester, NH (US)

(73) Assignee: DEKA PRODUCTS LIMITED PARTNERSHIP, Manchester, NH (US)

( * ) Notice: Subject to any disclaimer, the term of this patent is extended or adjusted under 35 U.S.C. 154(b) by 386 days.

This patent is subject to a terminal disclaimer.

(21) Appl. No.: 14/809,624

(22) Filed: Jul. 27, 2015

(65) Prior Publication Data

US 2015/0328017 A1    Nov. 19, 2015

Related U.S. Application Data

(63) Continuation of application No. 12/027,141, filed on Feb. 6, 2008, now Pat. No. 9,114,028.

(Continued)

(51) Int. Cl.
*A61F 2/54* (2006.01)
*A61F 2/58* (2006.01)

(Continued)

(52) U.S. Cl.
CPC .............. *A61F 2/54* (2013.01); *A61F 2/581* (2013.01); *A61F 2/582* (2013.01); *A61F 2/585* (2013.01);

(Continued)

(58) Field of Classification Search
CPC ...... A61F 2002/5067; A61F 2002/5069; A61F 2002/507; A61F 2002/6836; A61F 2/54–2/585

See application file for complete search history.

(56) References Cited

U.S. PATENT DOCUMENTS 3,987,498 A * 10/1976 Mason .................... A61F 2/582
                                                                    623/24
4,841,773 A      6/1989 Stewart
(Continued)

FOREIGN PATENT DOCUMENTS

WO        02/00158 A2    1/2002
WO     2009/155595 A2   12/2009

OTHER PUBLICATIONS

Invitation to Pay Additional Fees and, Where Applicable, Protest Fee including Partial Search Report from corresponding International Appln. No. PCT/US2016/043864 dated Nov. 11, 2016 (7 pages).

(Continued)

*Primary Examiner* — Marcia L Watkins
(74) *Attorney, Agent, or Firm* — McCormick, Pauding & Huber LLP

(57) ABSTRACT

A prosthetic arm apparatus comprising a plurality of interconnected segments that provide the prosthetic arm apparatus with substantially the same movement capability and function as a human arm. The segments are connected to one another and connectable to a harness mount that may be adorned by the user. Each segment of the plurality of (Continued)

segments includes an actuator providing a portion of the movement capability, and each segment may operate independently of each of the other segments of the plurality of segments. One segment of the plurality of segments includes a non-backdriving clutch that transfers power from the actuator to an output interface of the segment when the actuator is actuated to generate movement of the output interface in either of two opposing directions and prevents backward transfer of power from the output interface to the actuator of the segment in both of the two opposing directions.

18 Claims, 41 Drawing Sheets

Related U.S. Application Data

(60) Provisional application No. 60/963,639, filed on Aug. 6, 2007, provisional application No. 60/899,833, filed on Feb. 6, 2007.

(51) Int. Cl.
*A61F 2/70* (2006.01)
*A61F 2/76* (2006.01)
*A61F 2/78* (2006.01)
*A61F 2/68* (2006.01)
*A61F 2/50* (2006.01)
*A61F 2/30* (2006.01)

(52) U.S. Cl.
CPC ............... *A61F 2/586* (2013.01); *A61F 2/68* (2013.01); *A61F 2/78* (2013.01); *A61F 2002/30464* (2013.01); *A61F 2002/507* (2013.01); *A61F 2002/5061* (2013.01); *A61F 2002/5069* (2013.01); *A61F 2002/5083* (2013.01); *A61F 2002/543* (2013.01); *A61F 2002/546* (2013.01); *A61F 2002/587* (2013.01); *A61F 2002/6827* (2013.01); *A61F 2002/6836* (2013.01); *A61F 2002/6845* (2013.01); *A61F 2002/6854* (2013.01); *A61F 2002/6863* (2013.01); *A61F 2002/701* (2013.01); *A61F 2002/704* (2013.01); *A61F 2002/764* (2013.01); *A61F 2002/7625* (2013.01); *A61F 2002/7635* (2013.01); *A61F 2002/7862* (2013.01); *A61F 2220/0075* (2013.01)

(56) References Cited

U.S. PATENT DOCUMENTS

| | | | |
|---|---|---|---|
| 5,252,102 A | | 10/1993 | Singer et al. |
| 5,336,269 A | * | 8/1994 | Smits ................. A61F 2/72 623/24 |
| 5,617,595 A | | 4/1997 | Landi et al. |
| 5,748,845 A | | 5/1998 | Labun et al. |
| 5,881,609 A | * | 3/1999 | Palmer ............... B25B 13/462 192/43 |
| 6,344,062 B1 | * | 2/2002 | Abboudi ............. A61B 5/036 623/24 |
| 6,685,661 B2 | | 2/2004 | Peled |
| 8,430,578 B1 | | 4/2013 | Theriault |
| 9,114,028 B2 | * | 8/2015 | Langenfeld ........... A61F 2/54 |
| 10,092,423 B2 | | 10/2018 | Goldfarb et al. |
| 2003/0018388 A1 | * | 1/2003 | Comer ................. A61F 2/54 623/14.13 |
| 2004/0267379 A1 | | 12/2004 | Pasolini |
| 2005/0177952 A1 | | 8/2005 | Wilkinson et al. |
| 2005/0256507 A1 | * | 11/2005 | Long ................ A61B 1/00133 604/528 |
| 2006/0135883 A1 | | 6/2006 | Jonsson et al. |
| 2008/0078033 A1 | | 4/2008 | Wyatt et al. |

OTHER PUBLICATIONS

Lee et al., "A Composite Discrete/Continuous Control of Robot Manipulators", Apr. 1991, Carnegie Mellon University: The Robotics Institute, Pittsburg, PA, pp. 1-21.

* cited by examiner

ARM PROSTHETIC DEVICE

CROSS REFERENCE TO RELATED APPLICATIONS

This application is a continuation of U.S. patent application Ser. No. 12/027,141 filed Feb. 6, 2008, now U.S. Pat. No. 9,114,028, issued Aug. 25, 2015, which claims priority to U.S. Provisional Patent Application Ser. No. 60/899,833, filed Feb. 6, 2007 and U.S. Application Ser. No. 60/963,639, filed Aug. 6, 2007, each of which is hereby incorporated by reference in its entirety.

STATEMENT OF GOVERNMENT INTEREST

This invention was made with Government support under Contract Number W911 NF-06-C-001 awarded by the U.S. Army RDECOM ACQ CTR. The Government has certain rights in the invention.

TECHNICAL FIELD

The present development relates to mechanical and medical devices and, more particularly, to prosthetics. More particularly, the development utilizes mechanical structure and user or motor stimuli to operate the prosthesis similarly to a human limb.

BACKGROUND INFORMATION

Existing prosthetic arms having limited movement for the user. Further, there are limited options for those patients who have lost their entire arm, shoulder to hand. Also, hand portions of existing prosthetic arms give the user, in many instances, one degree of movement. These prosthetics give limited capability with respect to, amongst other things, finer tasks.

Accordingly, there is a need for a prosthetic that replaces an arm from shoulder to hand and that has increased degrees of freedom. There is also a need for a prosthetic hand that moves in a realistic manner.

SUMMARY

It is one aspect of the present device to provide a prosthetic that will allow the user improved range of motion, improved tactile capabilities, increased comfort for the user, and decreased reliance on manual positioning of the prosthesis.

In accordance with one aspect of the invention, the present device employs a compliant structure that incorporates a shoulder flexion joint, a shoulder abduction joint, a humeral rotator, an elbow flexion joint, a wrist rotation joint, and a wrist flexion joint. The present device also discloses a hand assembly.

In accordance with one embodiment of the device, the shoulder flexion joint assembly includes a motor, a belt, a pulley, a gear train, a harmonic drive, a potentiometer, a non-backdriving clutch, and a compliance sensor. The electrically driven motor rotor drives the belt that is defined by two pulleys. The first pulley is magnetically driven by the motor rotor. The second pulley is driven by the belt and engages the harmonic drive. The harmonic drive has an interior wave generator that corresponds with the flexible spline. The spline in turn engages the exterior circular spline, resulting in drastic reduction rates and driving the shoulder output flange, allowing the shoulder joint flexion movement.

In accordance with another aspect of the shoulder flexion joint, the joint assembly also discloses a clutch. The clutch has an input cage, an output hex, and a clutch race, or ground. When the shoulder flexion joint is acted upon by an output force, the output hex is engaged in a friction lock with the clutch race and bearings lining the exterior of the output hex, preventing backward transfer of power through the clutch.

In accordance with another aspect of the shoulder flexion joint, the joint assembly also discloses a shoulder compliance sensor. The sensor provides the shoulder flexion joint with measured compliance. The sensor utilizes the interior rim of the circular spline of the harmonic drive. The exterior rim of the circular spline additionally accommodates stationary reactor elements and series elastic elements. The circular spline, series elastic elements and reactor elements are circumferentially disposed around the interior of a clamp. Together, the clamp and a compliance reactor substantially enclose the circular spline, series elastic elements, and reactor elements. The clamp and compliance reactor remain stationary while the circular spline, series elastic elements, and reactor elements are rotatably disposed around the exterior rim of the spline. Additionally, a magnet is disposed on the exterior rim of the circular spline. Upon application of force, the position of the circular spline alters causing the series elastic elements to compress against the reactor elements. The movement of the reactor elements transmits the rotational displacement of the circular spline via the reactor movement in relation to the stationary magnet. In this manner, the compliance is built into the shoulder flexion joint and works to absorb energy when the joint is subjected to a load or an unexpected shock.

In accordance with the shoulder abduction joint, the joint features a shoulder flexion mount. The shoulder flexion joint fastens to the shoulder flexion mount. The abductor also discloses a harness mount.

The humeral rotator features a harmonic drive, a motor, a motor armature, a potentiometer and a humeral mount. The support structure of the humeral rotator has a humeral mount site at the output of the rotator. The motor drives the motor armature, which in turn drives the wave generator of the harmonic drive. The wave generator drives the interior flexible spline, which in turn interacts with the outer circular spline. The circular spline then drives the rotational movement of the humeral rotator.

In further accordance with an aspect of the humeral rotation site, the potentiometer features a position pot and a potentiometer shaft.

In accordance with another embodiment of the device, the elbow flexion joint is further comprised of a motor armature, a motor rotor, a motor rotor magnet integrated into the motor rotor, a sun gear also integrated into the motor rotor, four planet gears, a ring gear, a harmonic drive, and a potentiometer.

In accordance with another aspect of the elbow flexion joint, the motor armature applies electrical force to the motor rotor magnet integrated onto the surface of the motor rotor. The motor rotor in turn rotationally drives the sun gear also integrated on the motor rotor. The sun gear rotationally drives the four planet gears. The planet gears in turn react against the stationary ring gear to effect rotation of the carrier plate, providing the first stage of reduction.

In accordance with a further aspect of the elbow flexion joint, the carrier plate drives the harmonic drive wave generator. The harmonic drive has an interior wave generator that corresponds with the flexible spline. The spline in turn engages the exterior circular spline, resulting in drastic reduction rates and driving the elbow output, allowing the elbow flexion joint movement.

In accordance with a further aspect of the elbow flexion joint, the elbow flexion joint also discloses a compliance sensor. The sensor provides the elbow flexion joint with measured compliance. The sensor utilizes the interior rim of the circular spline of the harmonic drive. The exterior rim of the circular spline additionally accommodates stationary reactor elements and series elastic elements. The circular spline, series elastic elements and reactor elements are circumferentially disposed around the interior of a clamp. Together, the clamp and a compliance reactor substantially enclose the circular spline, series elastic elements, and reactor elements. The clamp and compliance reactor remain stationary while the circular spline, series elastic elements, and reactor elements are rotatably disposed around the exterior rim of the spline. Additionally, a magnet is disposed on the exterior rim of the circular spline. Upon application of force, the position of the circular spline alters causing the series elastic elements to compress against the reactor elements. The movement of the reactor elements transmits the rotational displacement of the circular spline via the reactor movement in relation to the stationary magnet. In this manner, the compliance is built into the elbow flexion joint and works to absorb energy when the joint is subjected to a load or an unexpected shock.

The wrist rotation site features a harmonic drive, a motor, a motor armature, and a potentiometer. The motor drives the motor armature, which in turn drives the wave generator of the harmonic drive. The wave generator drives the interior flexible spline, which in turn interacts with the outer circular spline. The circular spline then drives the rotational movement of the wrist rotator.

In further accordance with an aspect of the wrist rotation site, the potentiometer features a position pot and a potentiometer shaft.

The wrist flexion joint is further comprised of a motor, an output arm, a gear train, and a series of elastic elements. The wrist flexion joint is driven by a motor that in turn drives the gear train. A final stage-driven gear transfers power to the output arm. The output arm connects to the main wrist flexion joint by a pivot axle.

In further accordance with an aspect of the wrist flexion joint, the output arm contains series elastic elements, a compliance sensor magnet, and a drive arm. The exterior casing of the output arm encloses the drive arm, which features at one end of the arm an opening defined to accept the pivot axle. The opposing end of the arm includes a compliance magnetic sensor. Disposed laterally at either side of the drive arm is a series elastic element.

In accordance with another aspect of the present device, the hand assembly is comprised of structures replicating a thumb, an index finger, and the grouping of the middle, ring, and pinky fingers. The thumb structure is driven by two parallel actuators that provide the structure with two inputs and two outputs. The two parallel actuators give the thumb structure opposition movement with the index finger and lateral movement. The two actuators are connected in parallel and fixed to the interior structure of the hand assembly. The thumb structure also features a flexural element separating the base of the thumb structure from the load-bearing portion of the structure. The base portion of the structure houses a sensor measuring the displacement of the loaded portion of the thumb relative to the thumb structure rest position. The load-bearing portion of the thumb structure contains the magnet whose displacement the sensor measures. In one embodiment of the thumb structure, the flexural structure is provided by linear flexural elements. Another embodiment of the thumb structure provides for spiral flexural elements. The sensor measuring displacement allows a calculation of the compliance to the thumb in both directions. The measured compliance allows continuous measurement of the force applied to the thumb structure in both directions.

In accordance with another aspect of the present device, the index finger structure of the hand assembly contains a rotating element at the base of the index finger that drives the motion of the finger. The index finger structure is comprised of a base joint that is connected to the rotating element. The base joint supports the lower phalanx structure. The lower phalanx structure terminates at the middle joint. The middle joint then supports the middle phalanx structure. The middle phalanx structure terminates at the farthest joint. The farthest joint then supports the upper phalanx structure.

In further accordance with the present device, the index finger structure and its integrated phalanx structures are kinematically determinate based on the rotation of the base element. When driven by the rotating element, the index finger structure is constrained to follow a set trajectory, enabling precise dexterity of index finger movement. In this way, the user can rely on the fixed trajectory of the index finger to perform fine tasks, such as pinching or retrieving small objects. In another embodiment of the index finger, the middle phalanx structure is fixedly joined to the upper phalanx structure.

In accordance with another aspect of the present device, the middle, ring, and pinky finger structures (MRP structures) are integrated into the hand assembly. Each of the three structures originates with a base joint supporting a lower phalanx structure. Each lower phalanx structure terminates at a middle joint. Each middle joint then supports a middle phalanx structure. Each middle phalanx joint terminates at a farthest joint. Each farthest joint then supports an upper phalanx structure.

Each individual MRP structure features an indeterminate linkage between the base joint and middle joint, and a deterministic linkage between the middle joint and farthest joint. As a result, the base and middle joints of the individual finger structures will continue to operate until the joint motion is impeded. During a grasping action, the middle phalanx structure will continue to operate even if the base phalanx structure is impeded by the object being grasped. This indeterminate linkage assists in creating a conforming grasp for the hand structure and is enabled by the double differential of the MRP transmissions.

Additionally, the MRP structures have indeterminate gear sets allowing the three structures to move separately in order to grasp or conform around an obstacle. Two differential gear sets incorporated into the hand assembly structure drive the MRP structures. The first differential gear is driven by the actuator and has outputs at the rotating element of one finger structure and at the input of the second differential gear. The second differential gear has outputs at the rotating elements of the remaining fingers. As one actuator drives all three MRP structures separately, the MRP structures are linked and under-actuated. As a result of the differential gear assembly, if one MRP structure encounters an obstacle, it will stop, but the other MRP structures will still move freely until they encounter an obstacle.

In accordance with another aspect of the present device, a non-backdriveable clutch controls the reaction of the thumb structure, the index finger structure and the linked MRP structures to the application of an output load. This embodiment of the clutch provides that any output torque on the hand assembly will result in a friction lock of the clutch. In this embodiment, the output hex of the clutch locks against the input spline and the bearings disposed between the output and input. Further, this embodiment of the clutch provides that upon sufficient input torque, the clutch unlocks and allows additional input movement without the user having to manually reset the hand assembly.

In accordance with another aspect of the present device, a planetary gear stage transfers torque from the actuator to the output stage. The actuator drives the planetary stage's ring gear which, through interaction with the planet gears, drives the planet's carrier, which then drives the output stage. The sun gear is attached through a spring to ground. Any torque applied to the planetary stage will cause a displacement of the sun gear until the torque is balanced by the displacement of the spring. Thus, the spring stores elastic energy and increases the compliance of the index structure. The use of the spring attached to the sun gear allows measurement of load on the structures without the addition of a load cell.

In accordance with another embodiment of the present device, a stage driver and timing belt transfer torque to the index finger structure and the MPR structures. The stage driver transfers the torque to the timing belt, loosening one side of the timing belt and tightening the opposite side. In further accordance with the current device, a tensioner positioned between the stage driver and its corresponding pulley displaces as the tension of the timing belt changes. The tensioner displacement stores energy. Inference of the load applied to the structure can be based upon that displacement. The use of this tensioner allows measurement of load on the structures without the addition of a load cell. The tensioner additionally stores elastic energy and increases the compliance of the structures.

These aspects of the invention are not meant to be exclusive and other features, aspects, and advantages of the present invention will be readily apparent to those of ordinary skill in the art when read in conjunction with the appended claims and accompanying drawings.

The same compliance method is applied to the MRP drive, allowing it to store elastic energy.

BRIEF DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENTS

Figure 1:
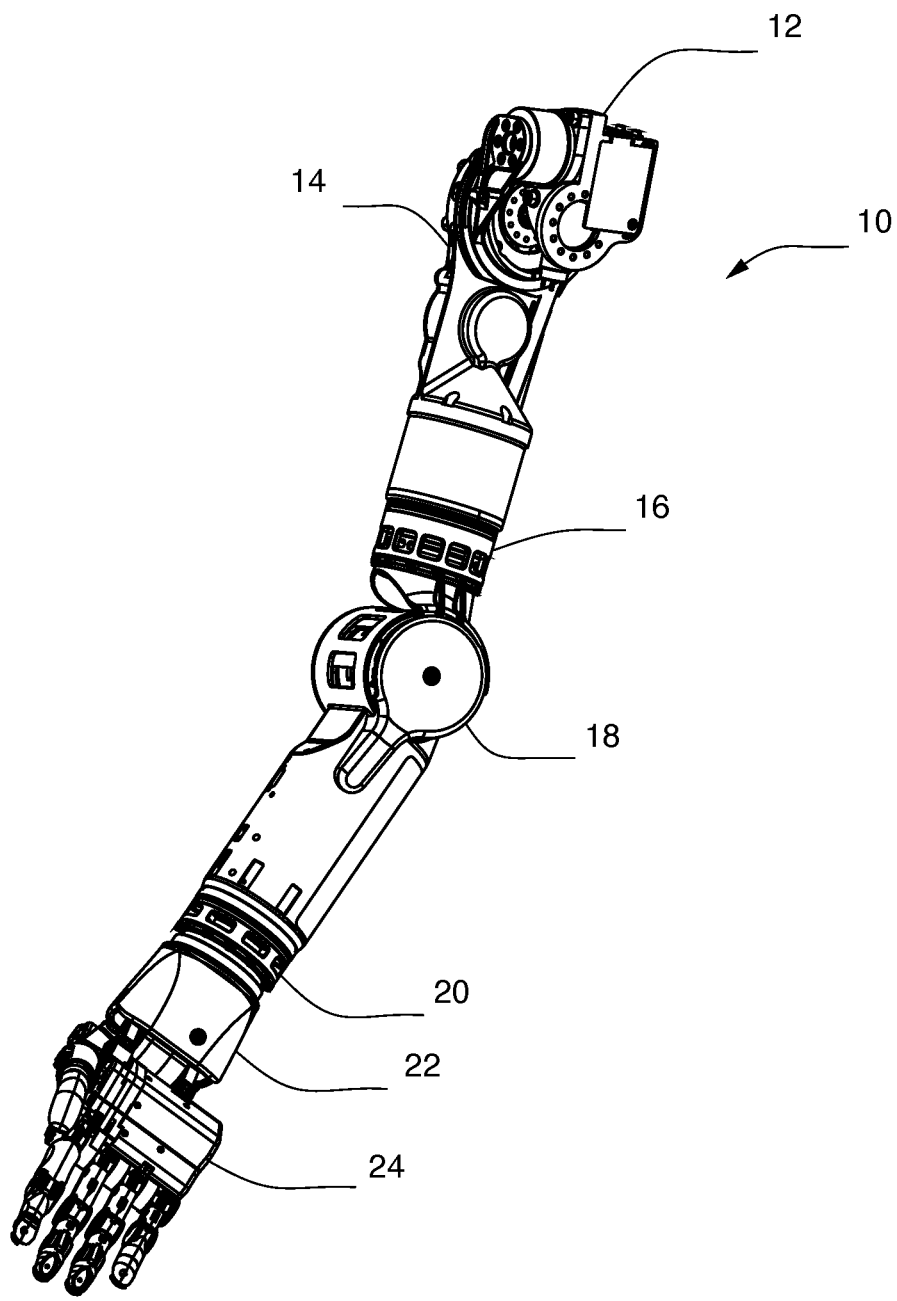
FIG. 1 is a perspective view of one embodiment of a prosthetic arm apparatus according to the present invention.
Figure 2:
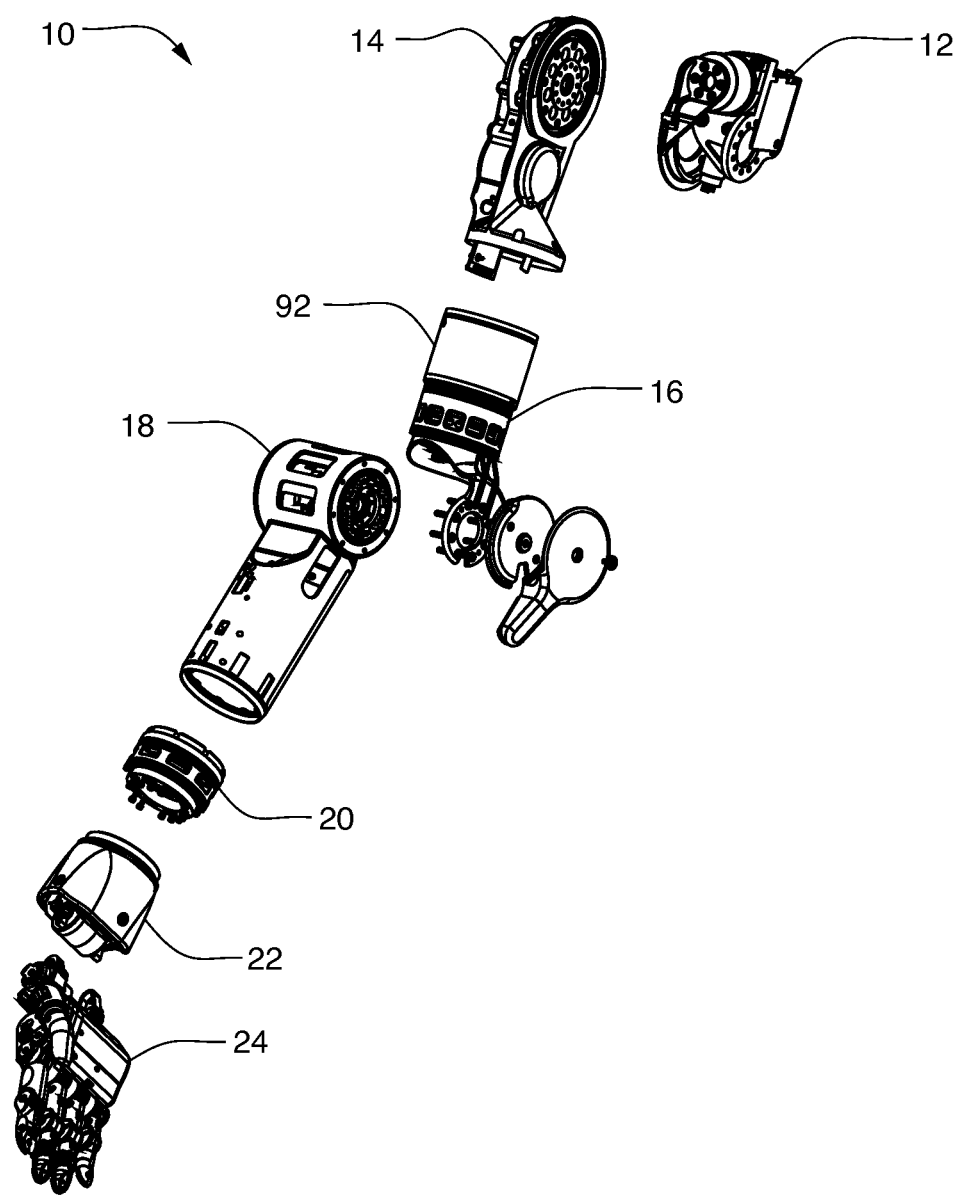
FIG. 2 is an exploded view of the prosthetic arm apparatus of FIG. 1.

Referring to FIGS. 1 and 2, a prosthetic arm apparatus 10 for attachment to a shoulder of a shoulder disarticulated amputee includes a plurality of segments, including a shoulder abductor 12, a shoulder flexion assembly 14, a humeral rotator 16, an elbow flexion assembly 18, a wrist rotator 20, a wrist flexion assembly 22, and a hand assembly 24. The prosthetic arm apparatus 10, in the exemplary embodiment, has the dimensions and weight of a female arm of a fiftieth percentile, so that many different users may comfortably use the prosthetic arm apparatus 10. As should be understood by those skilled in the art, the prosthetic arm apparatus 10 may be constructed to larger or smaller dimensions if desired.

Figure 3:
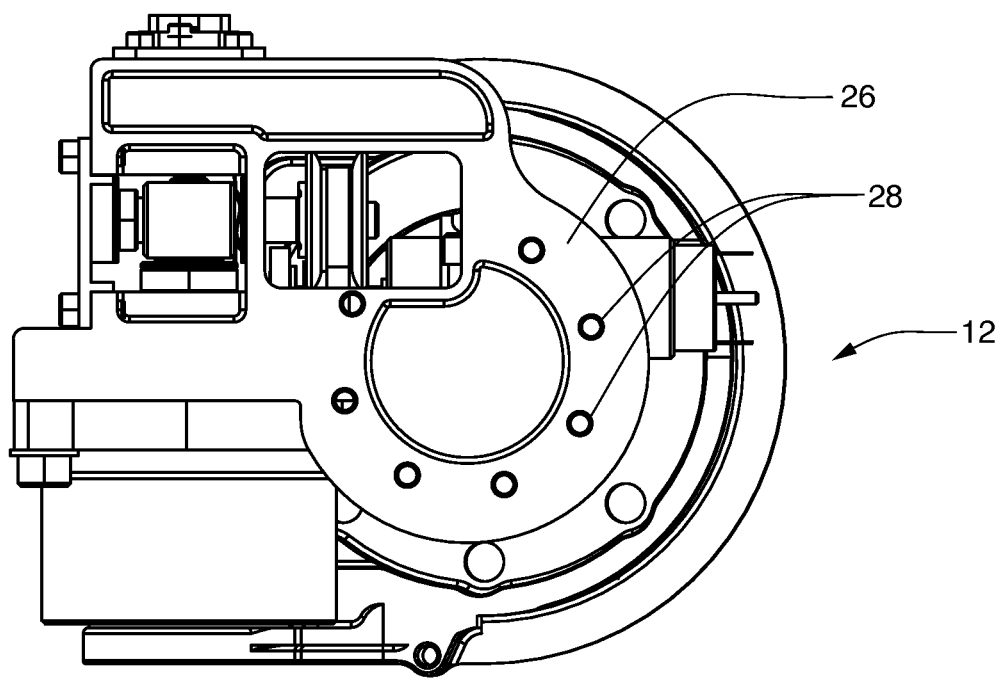
FIG. 3 is a rear view of a shoulder abductor of the prosthetic arm apparatus of FIG. 1 according to the present invention.

Referring to FIG. 3, one embodiment of the shoulder abductor 12 is shown. The shoulder abductor 12 includes a harness mount 26. The harness mount 26 has harness interface holes 28 that may be used to attach the abductor 12 to a prosthetic harness (not shown) or other system for supporting the prosthetic arm apparatus 10. In the exemplary embodiment, the harness may be one disclosed in co-pending U.S. patent application Ser. No. 12/026,971, by Altobelli, et al., entitled Dynamic Support Apparatus filed on Feb. 6, 2008, which is hereby incorporated by reference.

Figure 4:
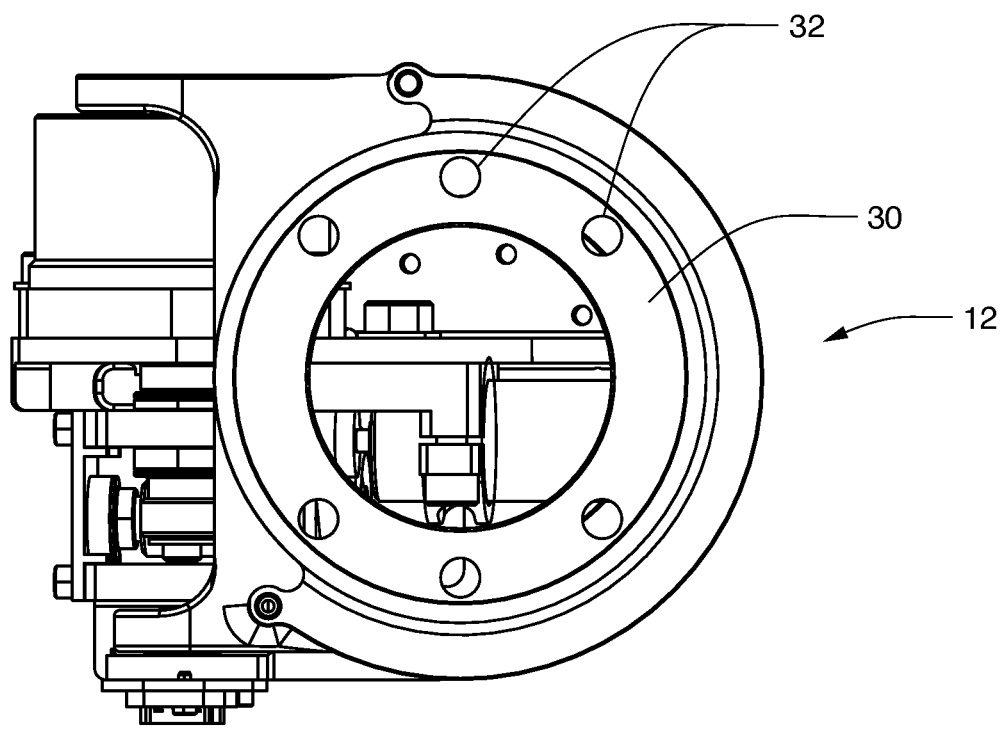
FIG. 4 is a front view of the shoulder abductor of FIG. 3.

Referring to FIG. 4, the shoulder abductor 12 also has a shoulder flexion assembly mount 30, shown according to one embodiment. The shoulder flexion assembly mount 30 interfaces with the shoulder flexion assembly 14 to mount the shoulder flexion assembly 14 onto the shoulder abductor 12. In one embodiment, the flexion assembly mount 30 has interface holes 32 to facilitate connection of the shoulder flexion assembly 14 by attachment means such as bolts.

Figure 5:
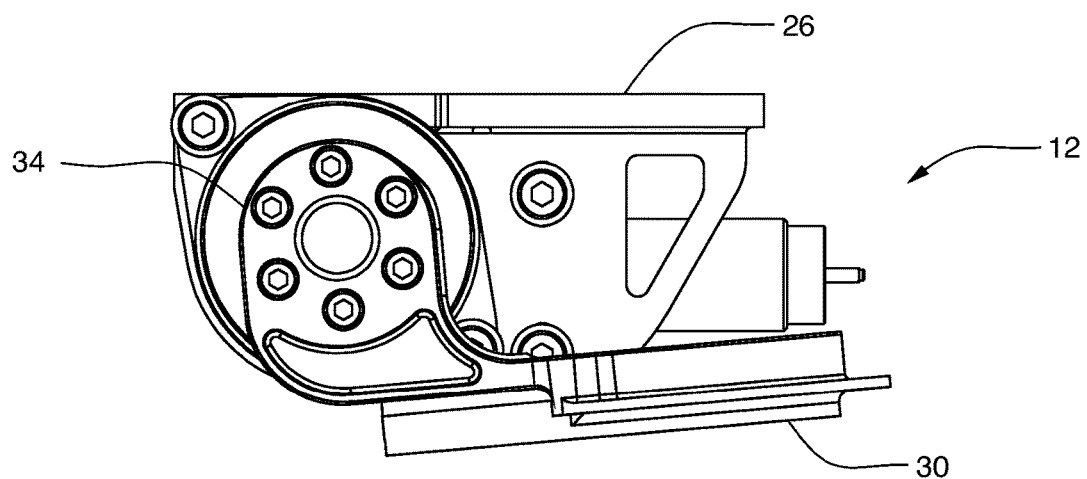
FIG. 5 is a side view of the shoulder abductor of FIG. 3.

Referring to FIG. 5, the shoulder abductor 12 further includes an abductor joint 34, shown according to one embodiment. The abductor joint 34 is used to pivot the shoulder flexion assembly mount 30 away from the harness mount 26 and back toward the harness mount 26.

Figure 6:
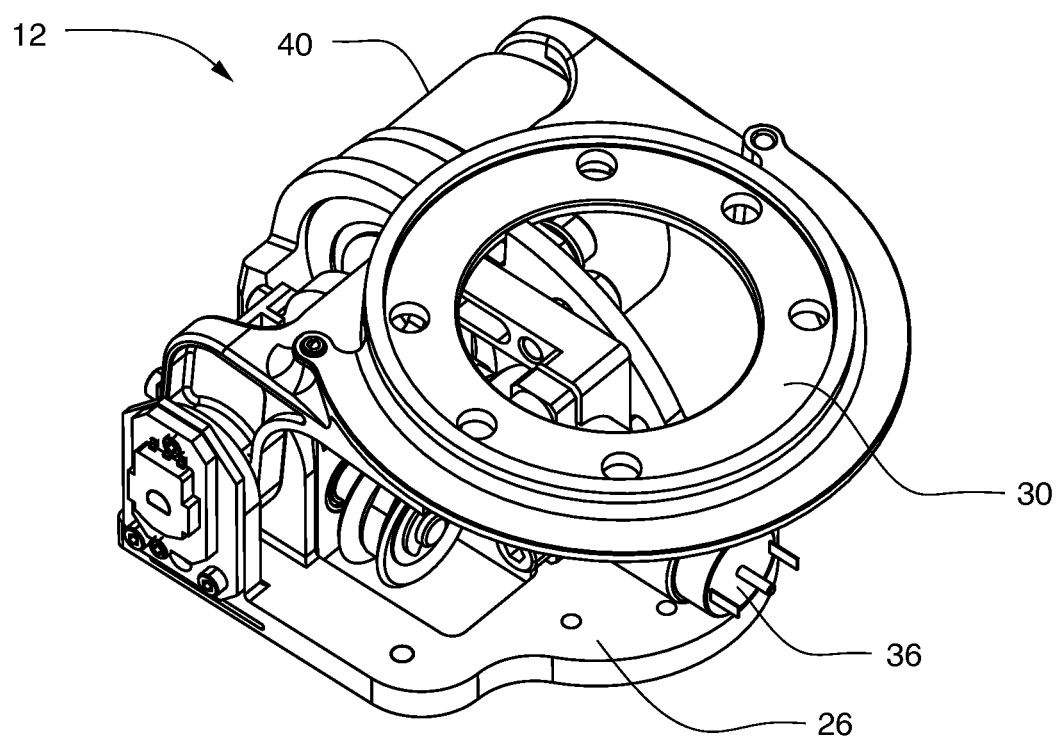
FIG. 6 is a perspective view of the shoulder abductor of FIG. 3.
Figure 7:
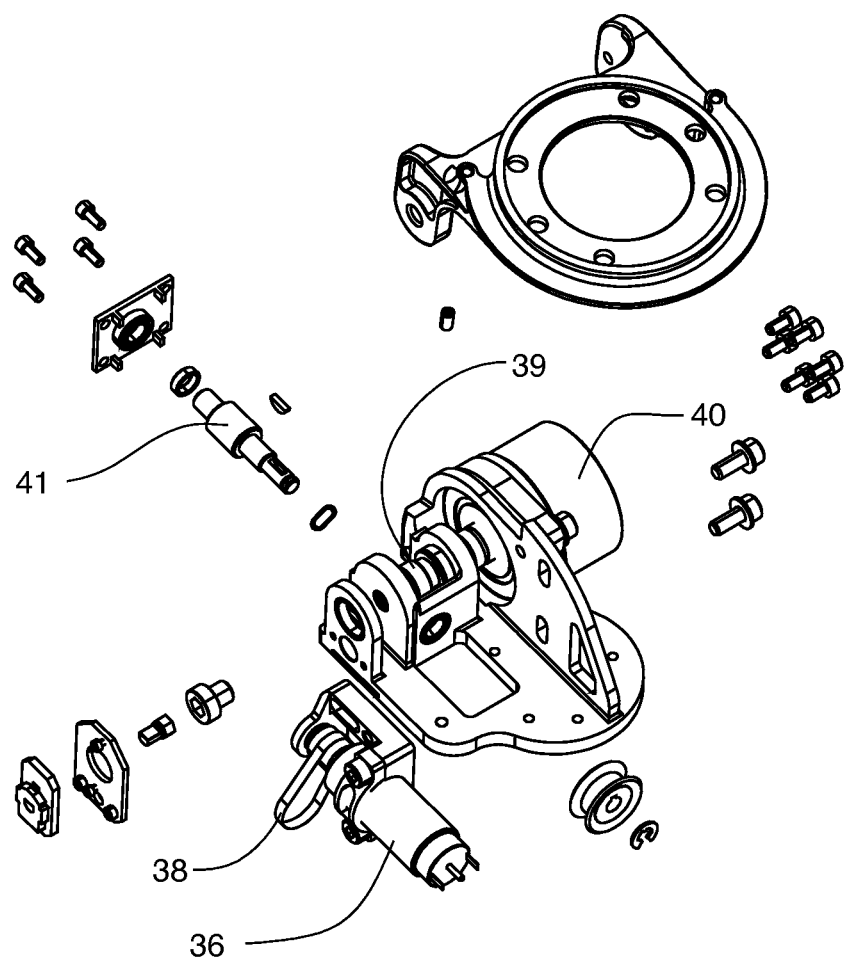
FIG. 7 is an exploded perspective view of the shoulder abductor of FIG. 6.

Referring to FIGS. 6 and 7, the shoulder abductor 12 includes an abductor motor 36 to control the pivotal movement of the abductor joint 34, both the shoulder abductor 12 and abductor motor 36 shown according to one embodiment. In this embodiment, the abductor motor 36 is a brushed DC motor controlling the pivotal movement through an abductor belt 38 connected to a worm drive 41 driving a worm wheel 39 connected to an abductor harmonic drive 40.

Figure 8:
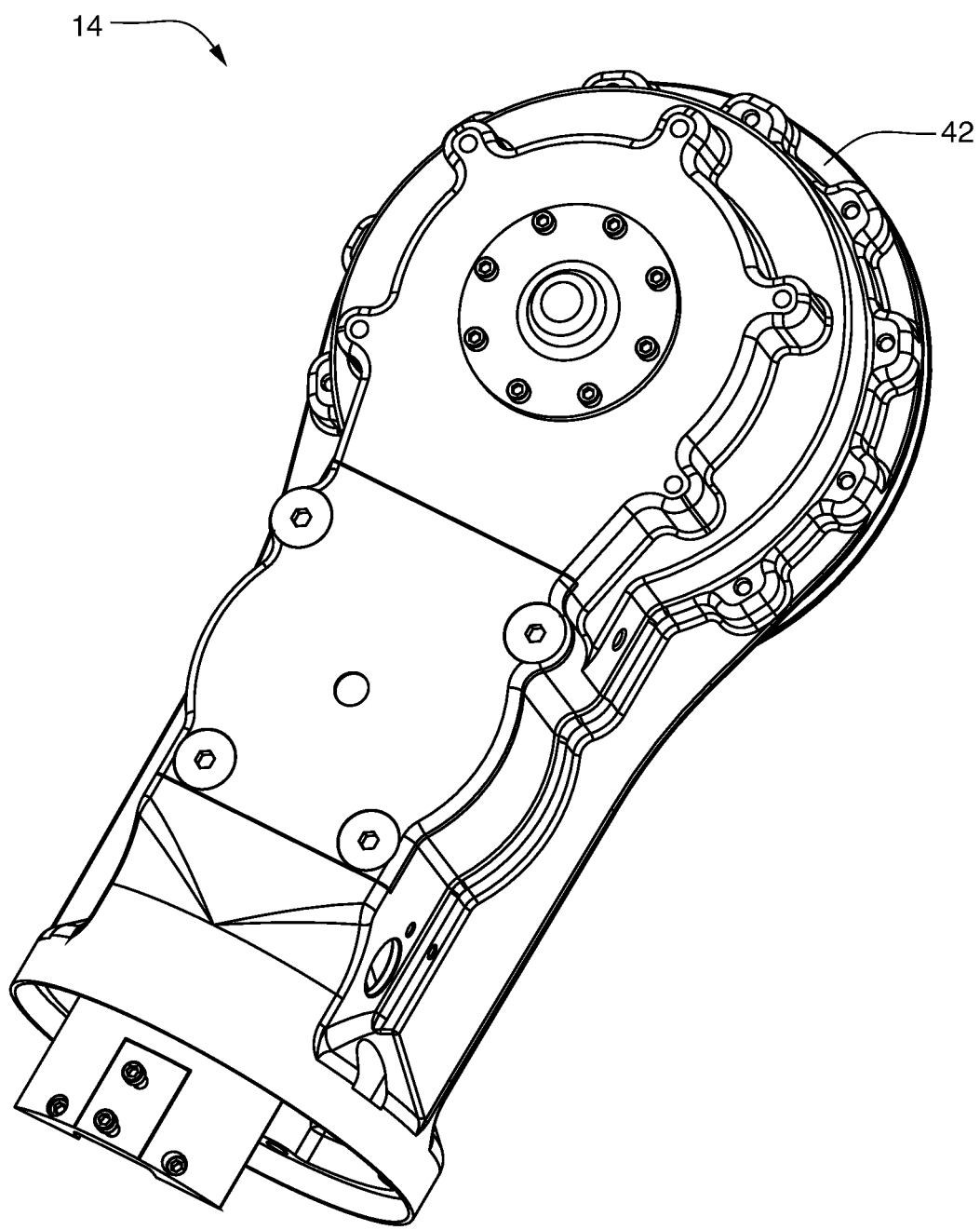
FIG. 8 is a perspective view of a shoulder flexion assembly of the prosthetic arm apparatus of FIG. 1 according to the present invention.
Figure 9:
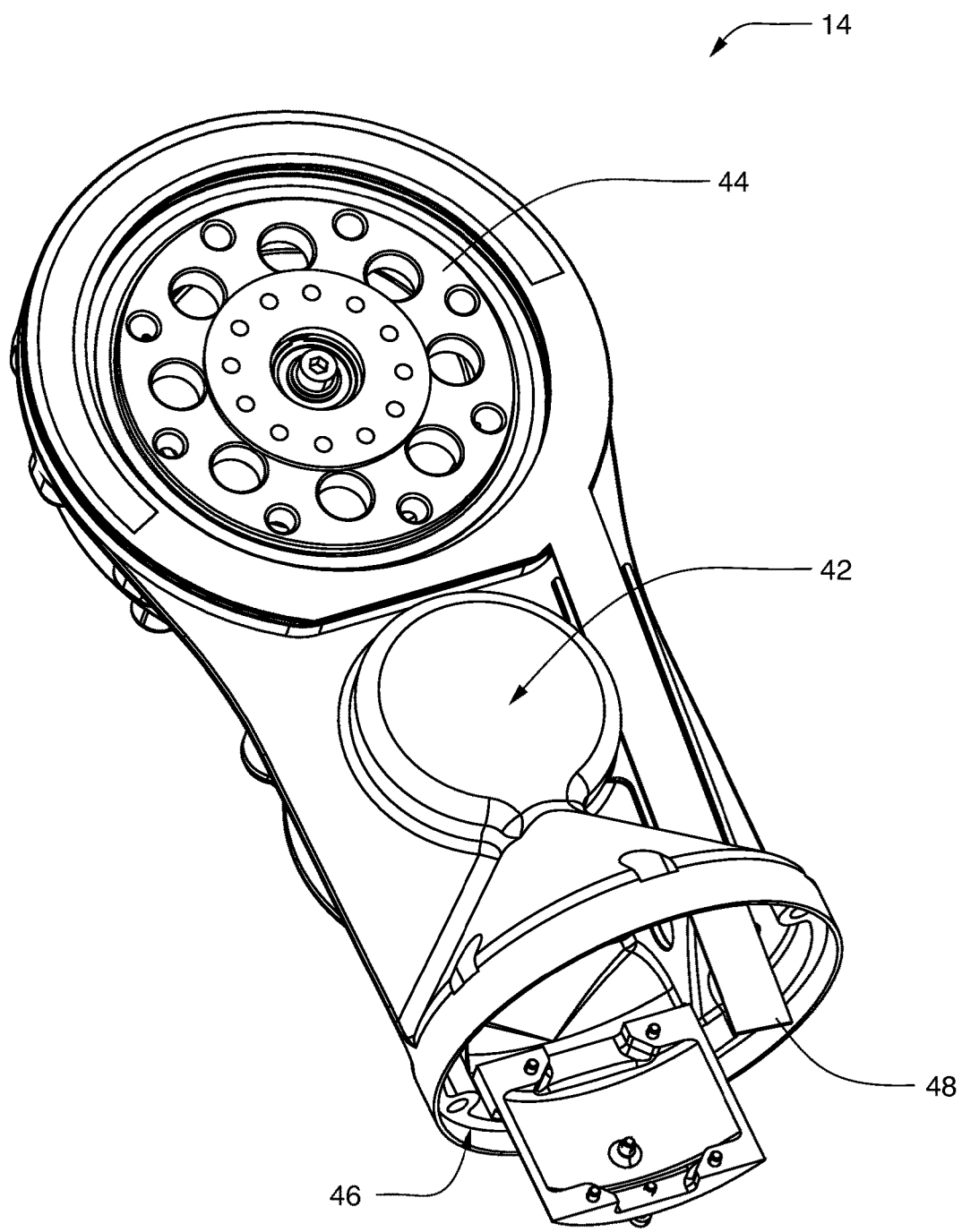
FIG. 9 is a reverse perspective view of the shoulder flexion assembly of FIG. 8.

Referring to FIGS. 8 and 9, the shoulder flexion assembly 14, in one embodiment, has a main shoulder housing 42, with an abductor interface 44 for connecting the shoulder flexion assembly 14 to the shoulder abductor 12. The shoulder flexion assembly 14 also has a humeral interface 46 for connecting the humeral rotator 16 to the shoulder flexion assembly 14.

Figure 10:
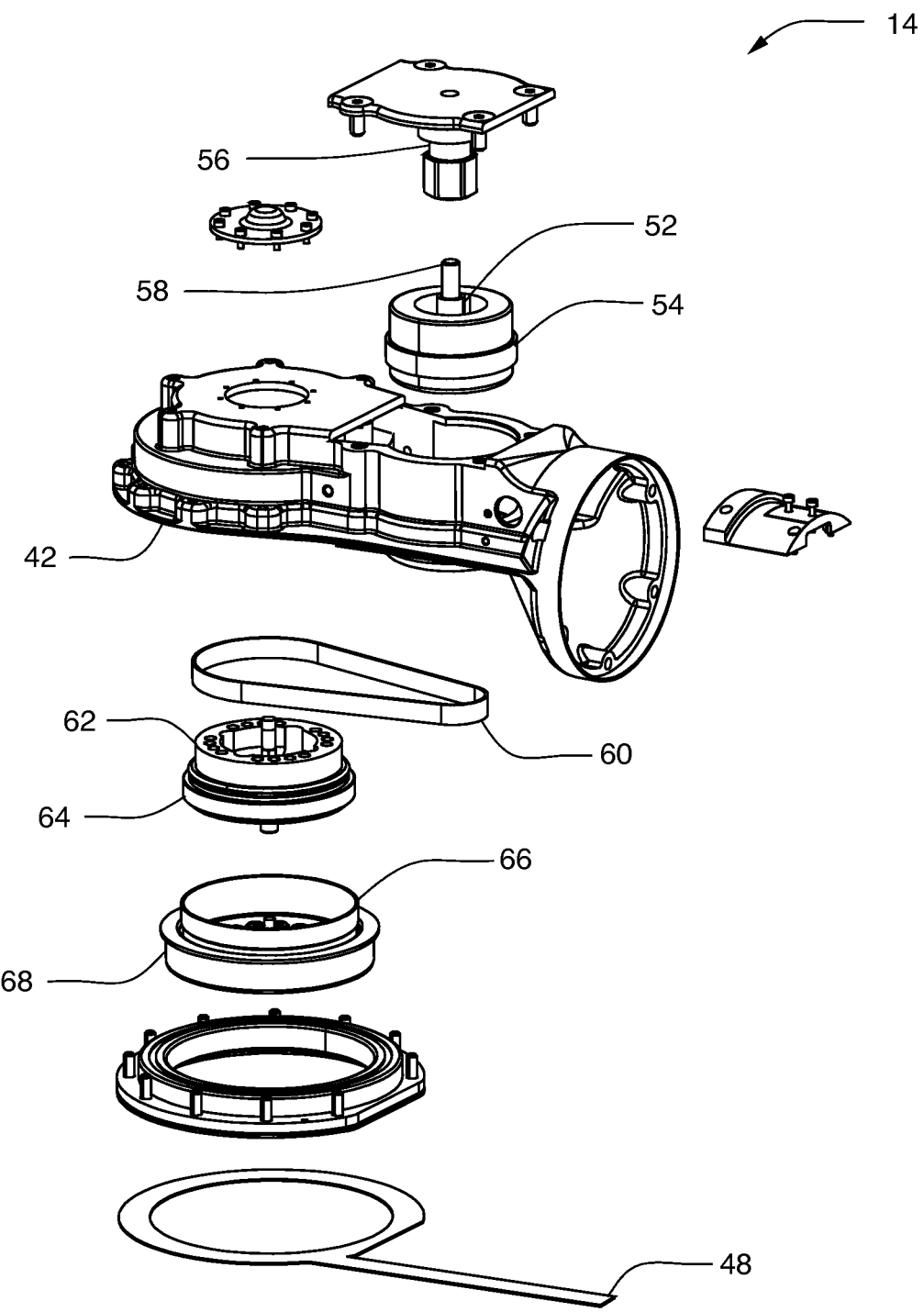
FIG. 10 is an exploded perspective view of the shoulder flexion assembly of FIG. 8.
Figure 11:
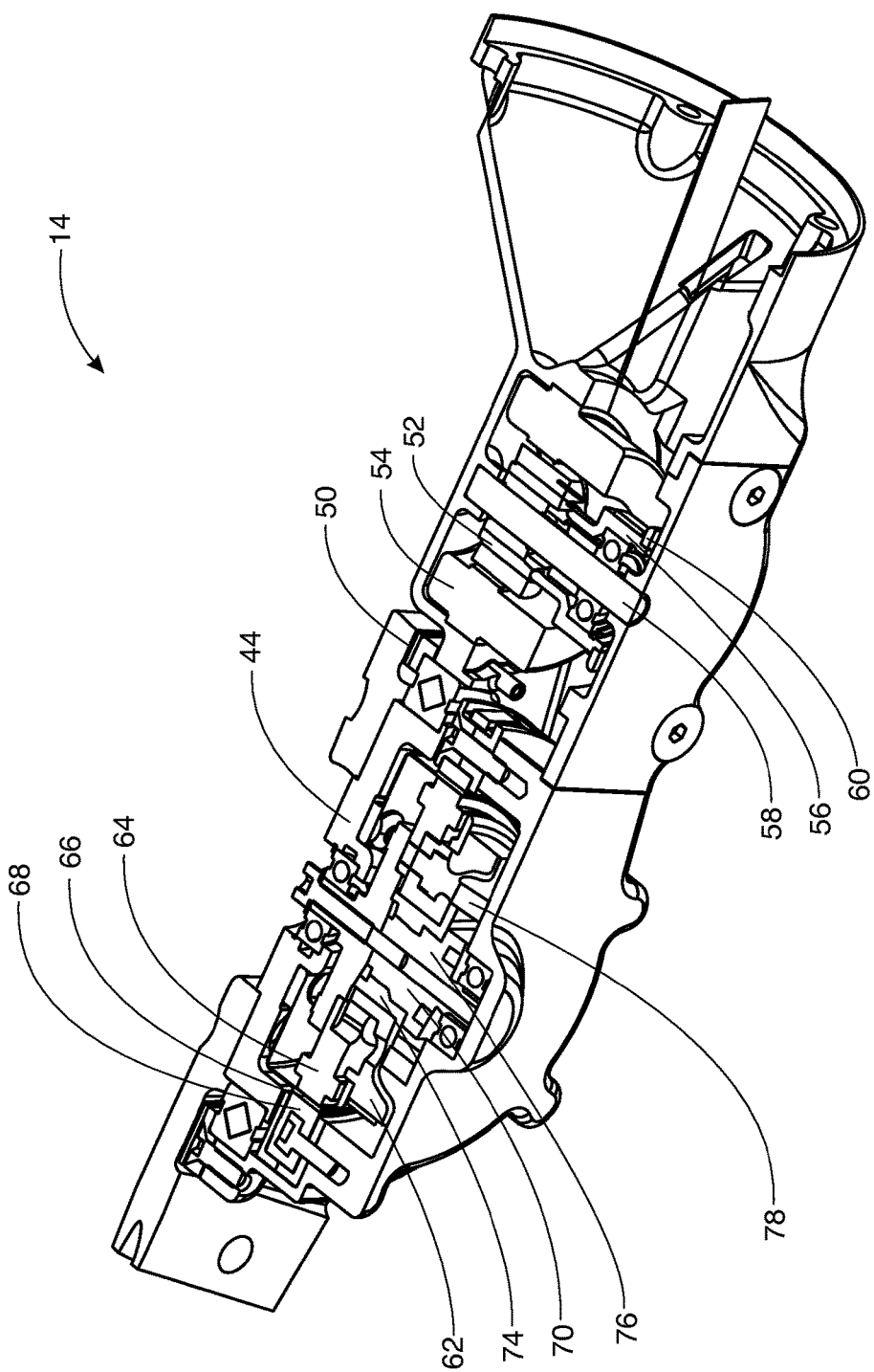
FIG. 11 is a cross-sectional perspective view of the shoulder flexion assembly of FIG. 8.

Referring to FIGS. 10 and 11, in one embodiment, shoulder flexion motor magnets 52 are disposed around an exterior 58 of a shoulder flexion motor rotor 54. In this embodiment, a shoulder flexion motor armature 55 drives the shoulder flexion motor rotor 52, which in turn drives a shoulder flexion motor pulley 56 around a motor shaft 58. The shoulder flexion motor pulley 56 supports a shoulder flexion belt 60, which is linked between the shoulder flexion motor pulley 56 and a shoulder flexion belt-driven pulley 62. The shoulder flexion belt-driven pulley 62 drives a shoulder flexion harmonic drive wave generator 64. A shoulder flexion harmonic drive flexspline 66 rotates against the shoulder flexion harmonic drive wave generator 64 and a shoulder flexion harmonic drive circular spline 68, resulting in reduced speed for the joint movement. The shoulder flexion harmonic drive flexspline 66 is connected to the abductor interface 44, and is thus able to rotate the shoulder flexion assembly 14 in reference to the abductor interface.

Referring to FIG. 11, in one embodiment, a non-backdriving clutch 70 is disposed inside the main shoulder housing 42. The non-backdriving clutch 70 allows the prosthetic arm 10 to hold position by locking when the prosthetic arm 10 is not moving.

Figure 12:
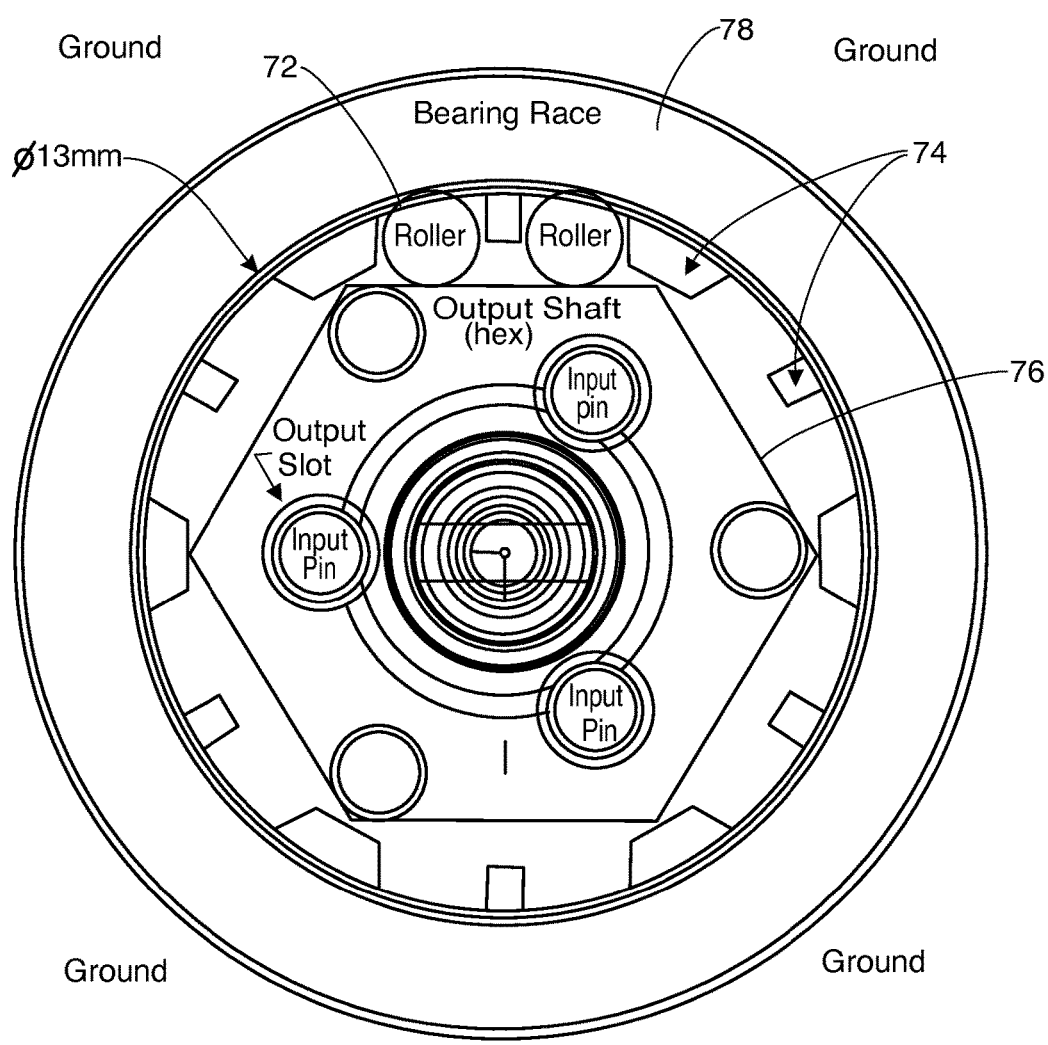
FIG. 12 is a top view of a non-backdriving clutch according to the present invention.

Referring to FIG. 12, in one embodiment, roller bearings 72 line the interface between an input cage 74 and an output hex 76. When a force is applied to the shoulder abductor interface 44, the output hex 76 locks against the bearing race 78 and the roller bearings 72. This prevents the shoulder flexion assembly 14 from moving due to force applied to its output, shoulder abductor interface 44. Upon the exertion of a necessary amount of input force through the clutch input cage 74, the output hex 76 disengages and allows the shoulder flexion assembly 14 to move. The clutch input cage 74 and the output hex 76 are both constrained by a clutch race 78. It should be understood by those skilled in the art, that other mechanisms could be used to prevent backdriving of the prosthetic arm 10, such as a clutch that locks in one direction or a solenoid with brakes that engage when the solenoid is powered.

Figure 13:
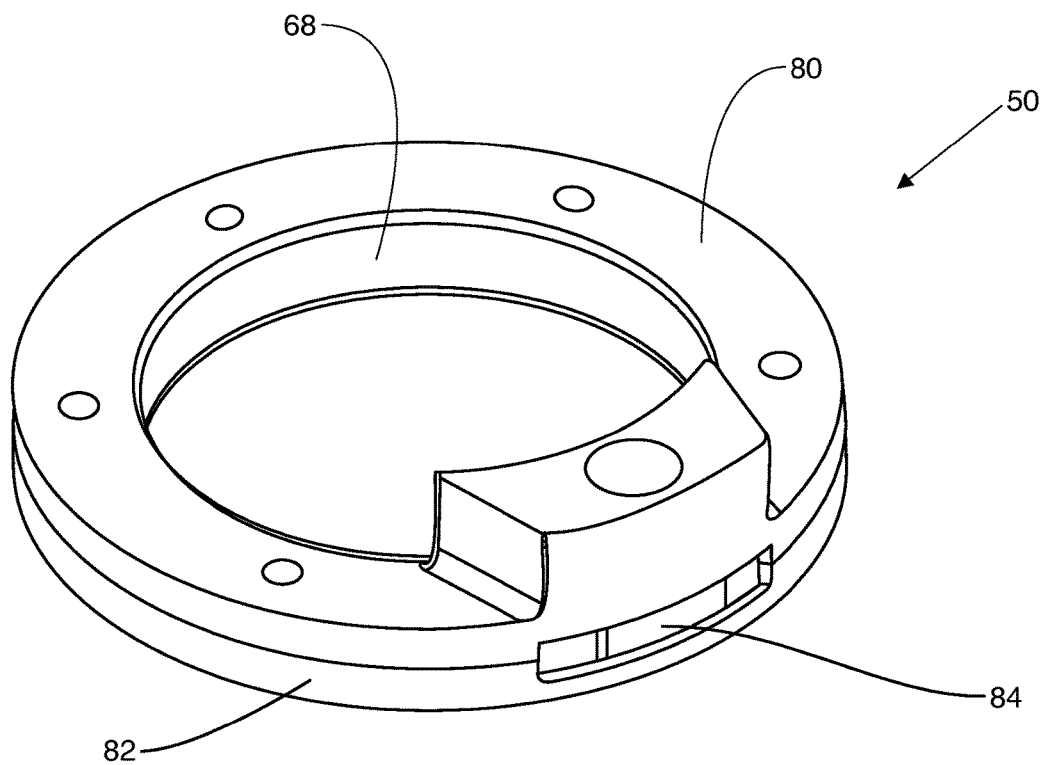
FIG. 13 is a perspective view of a fully assembled compliance subassembly of the shoulder flexion assembly of FIG. 8.

Referring to FIG. 13, in one embodiment, a compliance subassembly 50 includes a compliance reactor 80 positioned on top of the shoulder flexion harmonic drive circular spline 68 and held in place by the clamp 82. The compliance reactor 80 measures the amount of displacement in the compliance subassembly 50 in relation to the position of a compliance sensor magnet 84.

Figure 14:
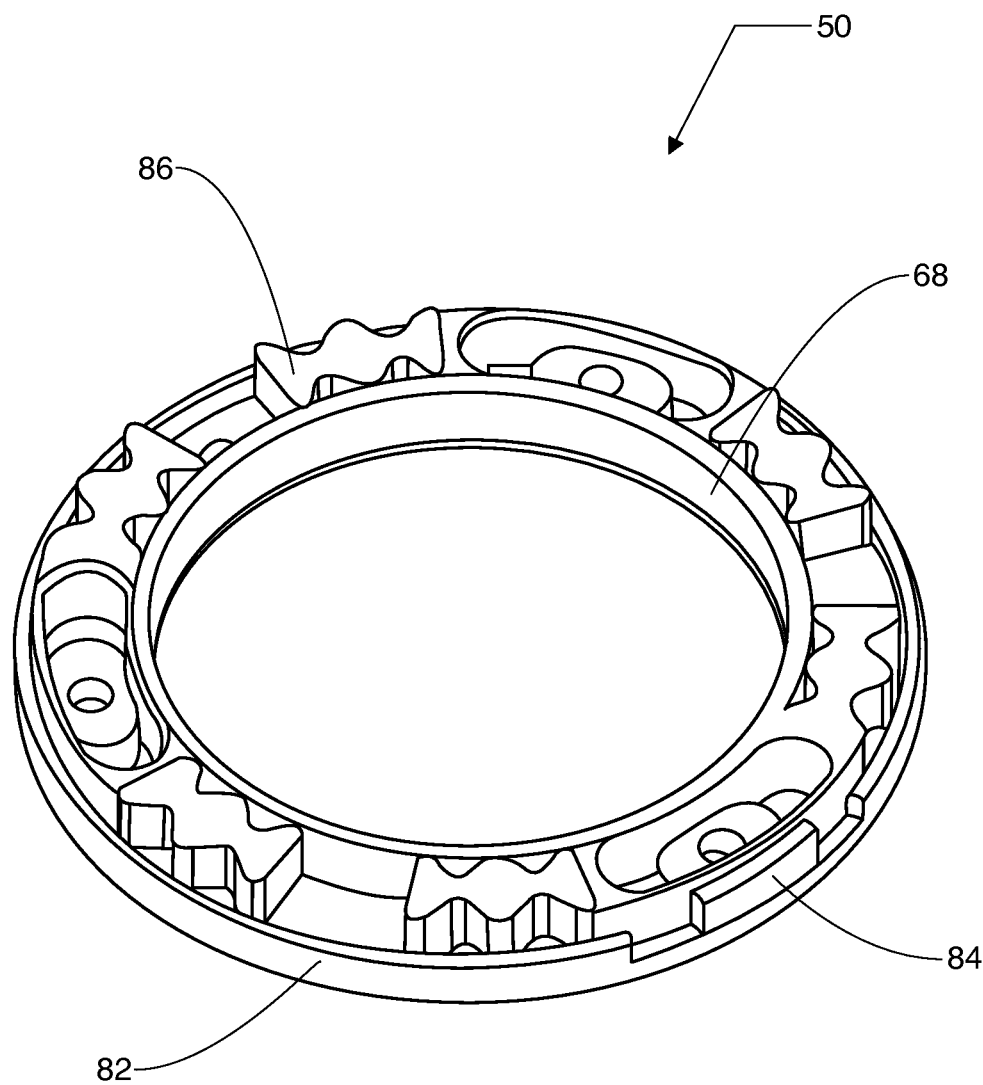
FIG. 14 is a perspective view of the bottom portion of the compliance subassembly of FIG. 13.

Referring to FIG. 14, in one embodiment, the interior of compliance subassembly 50 includes series elastic elements 86. The shoulder flexion harmonic drive circular spline 68 defines the interior of the compliance subassembly 50 and is formed to accommodate the placement of the series elastic elements 86 around an outer diameter 87 of the shoulder flexion harmonic drive circular spline 68. The series elastic elements 86 are confined by the shoulder flexion harmonic drive circular spline 68 and the clamp 82.

Figure 15:
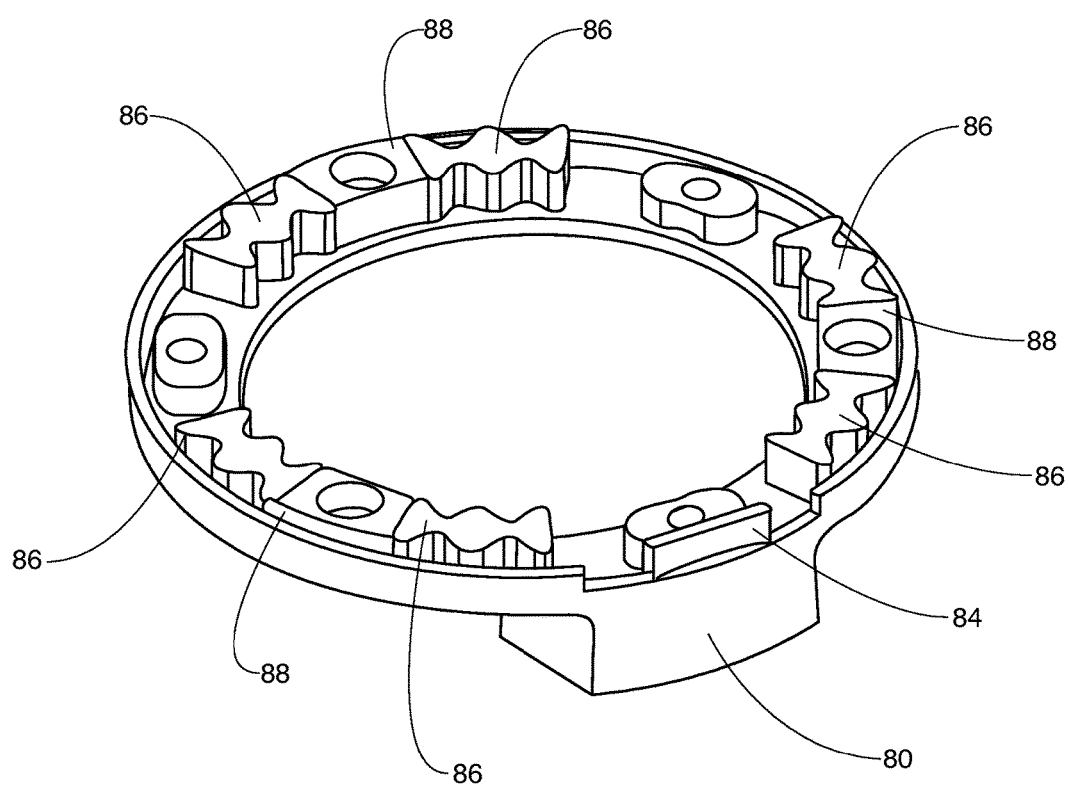
FIG. 15 is a perspective view of the top portion of the compliance subassembly of FIG. 13.

Referring to FIG. 15, the placement of the compliance reactor 80 in relation to the series elastic elements 86 and reactor elements 88 is shown. In this embodiment, three reactor elements 88 are positioned around the compliance reactor 80, equidistant to each other. One series elastic element 86 is placed on either side of each reactor element 88. When the shoulder flexion assembly 14 is subjected to unexpected force, such as a sudden jolt or impact, the compliance reactor 80 and reactor elements 88 displace from their rest positions and compress against the series elastic elements 86. In that way, the compliance subassembly 50 attenuates the shock being transferred to the rest of the shoulder flexion assembly 14. The compliance reactor 80 may also measure the amount of displacement and compliance by measuring the movement of the compliance reactor 80 in relation to the stationary position of the compliance sensor magnet 84.

Figure 16:
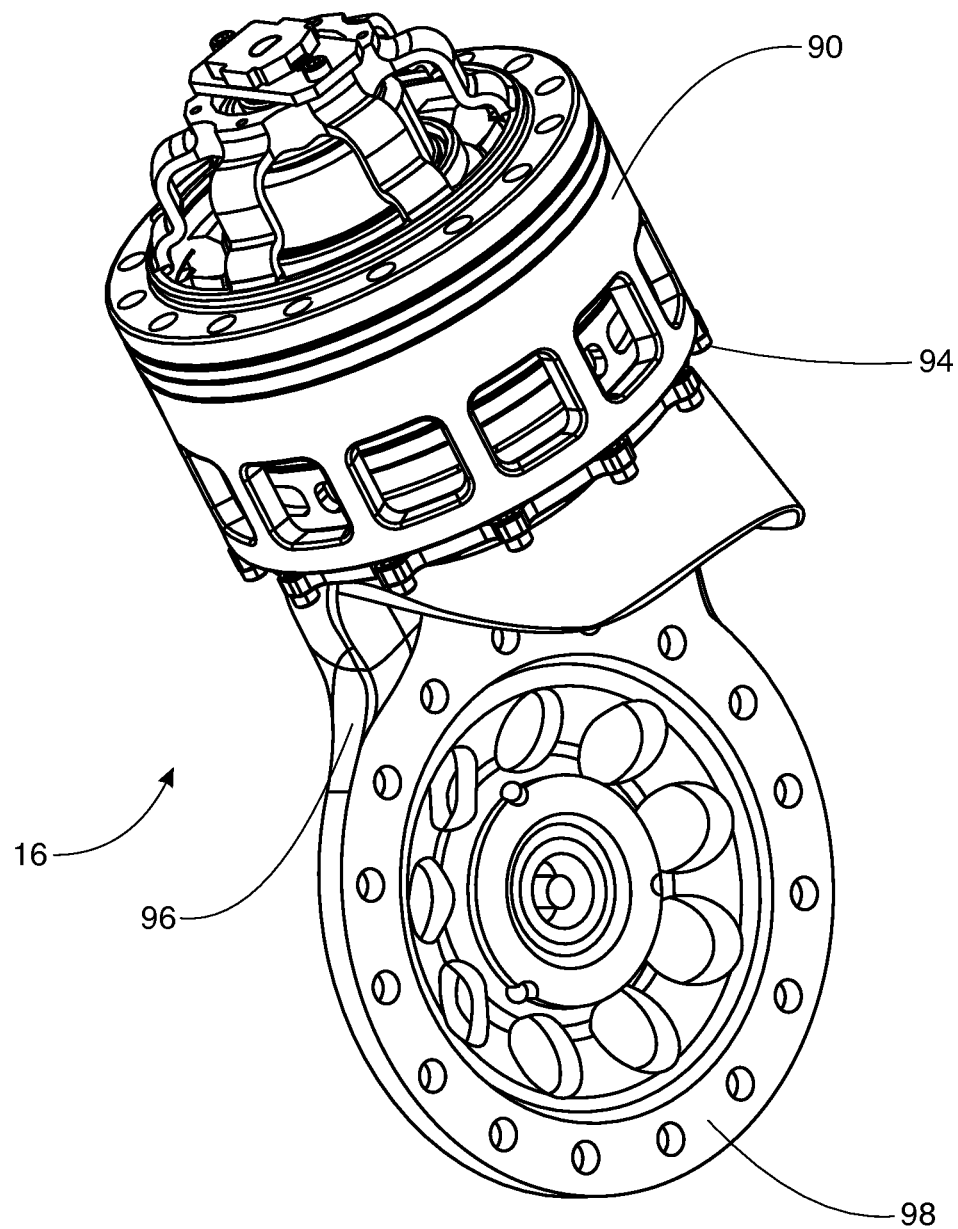
FIG. 16 is a perspective view of a humeral rotator of the prosthetic arm apparatus of FIG. 1 according to the present invention.

Referring to FIG. 16, one embodiment of the humeral rotator 16 is shown. The humeral rotator 16 includes an outer bearing carrier 90 and an arm control module 51 (FIG. 2). The first control housing 92 is used to connect the humeral rotator 16 to the shoulder flexion assembly 14 and may house electronic controllers for the plurality of segments. The inner rotational elements of the humeral rotator are held in place by a clamp 94, which is fastened to the outer bearing carrier 90. A humeral mount 96 passes through the clamp 94 and includes an elbow interface 98 for attaching the elbow flexion assembly 18 to the humeral rotator 16.

Figure 17:
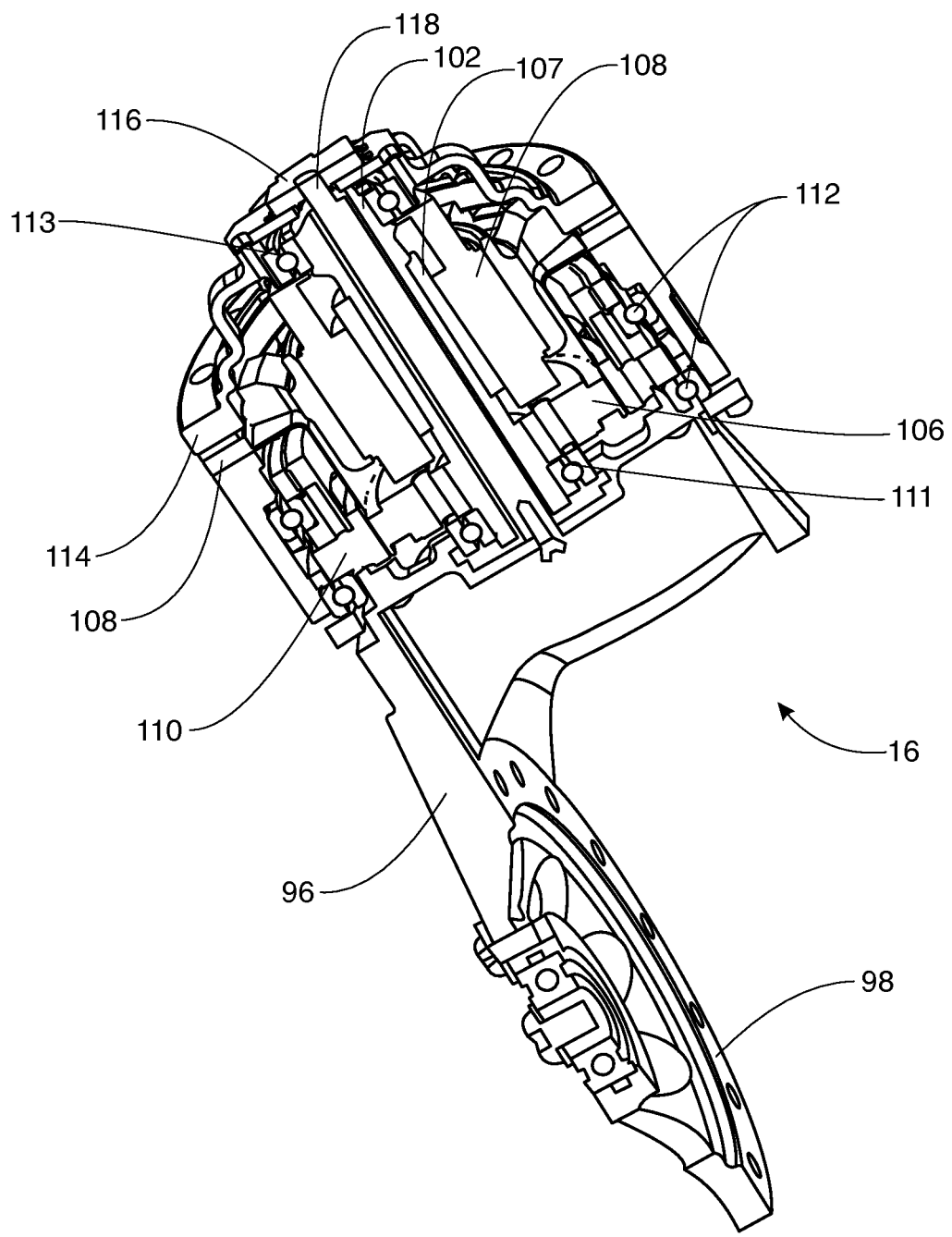
FIG. 17 is a cross-sectional perspective view of the humeral rotator of FIG. 16.

FIG. 17 shows a cross-sectional view of the humeral rotator 16. A humeral motor armature 100 drives a humeral motor rotor 102 having humeral magnets 104 disposed on its surface. The lower portion of the motor rotor 102 engages a humeral harmonic drive wave generator 106. A humeral harmonic drive flexspline 108 rotates with the humeral harmonic drive wave generator 106 against the humeral harmonic drive circular spline 110, resulting in a speed of rotation reduction as the humeral harmonic drive flexspline 108 causes the humeral mount 96 to move. Bearings 111 and 113 support the humeral motor rotor 102. Bearings 106 support the harmonic drive components 106, 108, 110. A bearing support 114 caps the outer bearing carrier 90 between the outer bearing carrier 90 and the first control housing 92.

Still referring to FIG. 17, the one embodiment, a humeral potentiometer 116 of the humeral rotator 16, measures the rotational displacement of a humeral potentiometer shaft 118 that rotates proportionately to the humeral mount 96.

Figure 18:
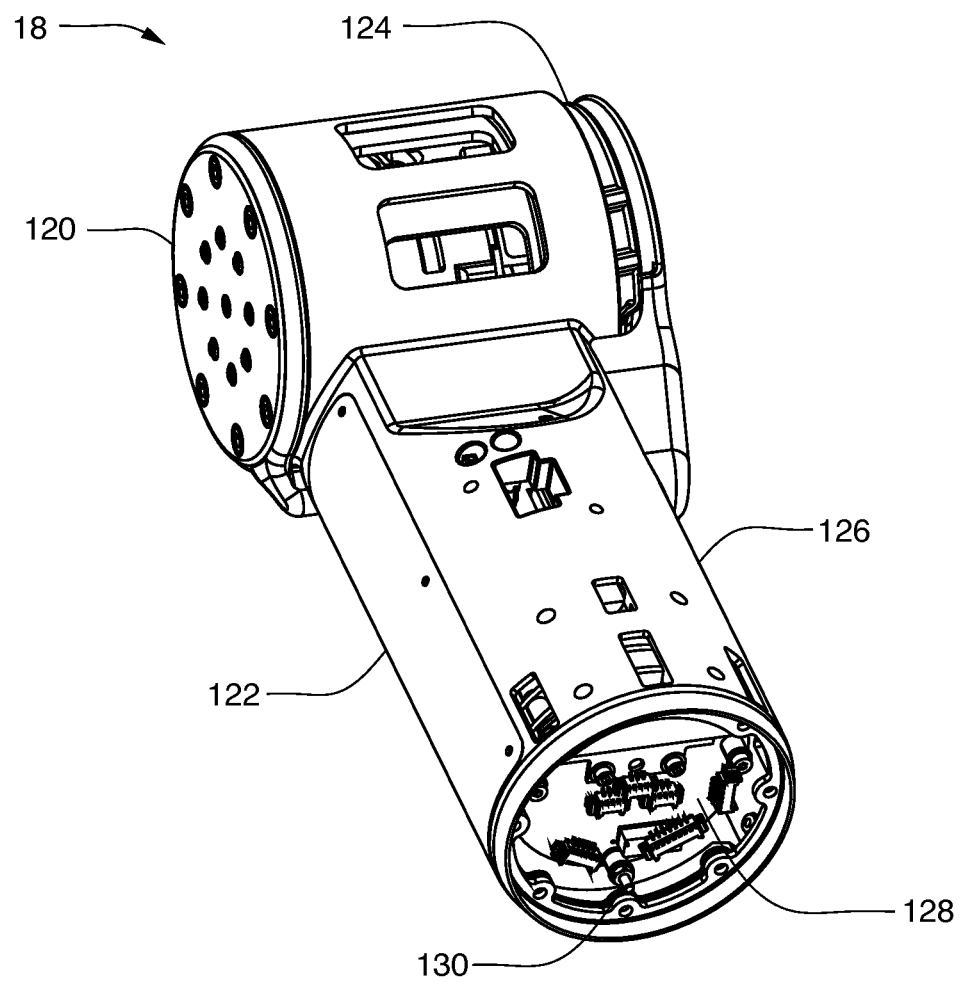
FIG. 18 is a perspective view of an elbow flexion assembly of the prosthetic arm apparatus of FIG. 1 according to the present invention.

Referring to FIG. 18, the elbow flexion assembly 18 includes an elbow joint 120 and a radial mount 122. The elbow joint 120 includes a slot 124 into which the elbow interface 98 of the humeral rotator is inserted to facilitate connection of the elbow flexion assembly 18 to the humeral rotator 16. The radial mount 122 provides a second electronics housing 126 for electronic controllers for the plurality of segments, in which an ACM stack 128 is located. The radial mount 122 includes a wrist interface 130, for attachment of the wrist rotator 20.

Figure 19:
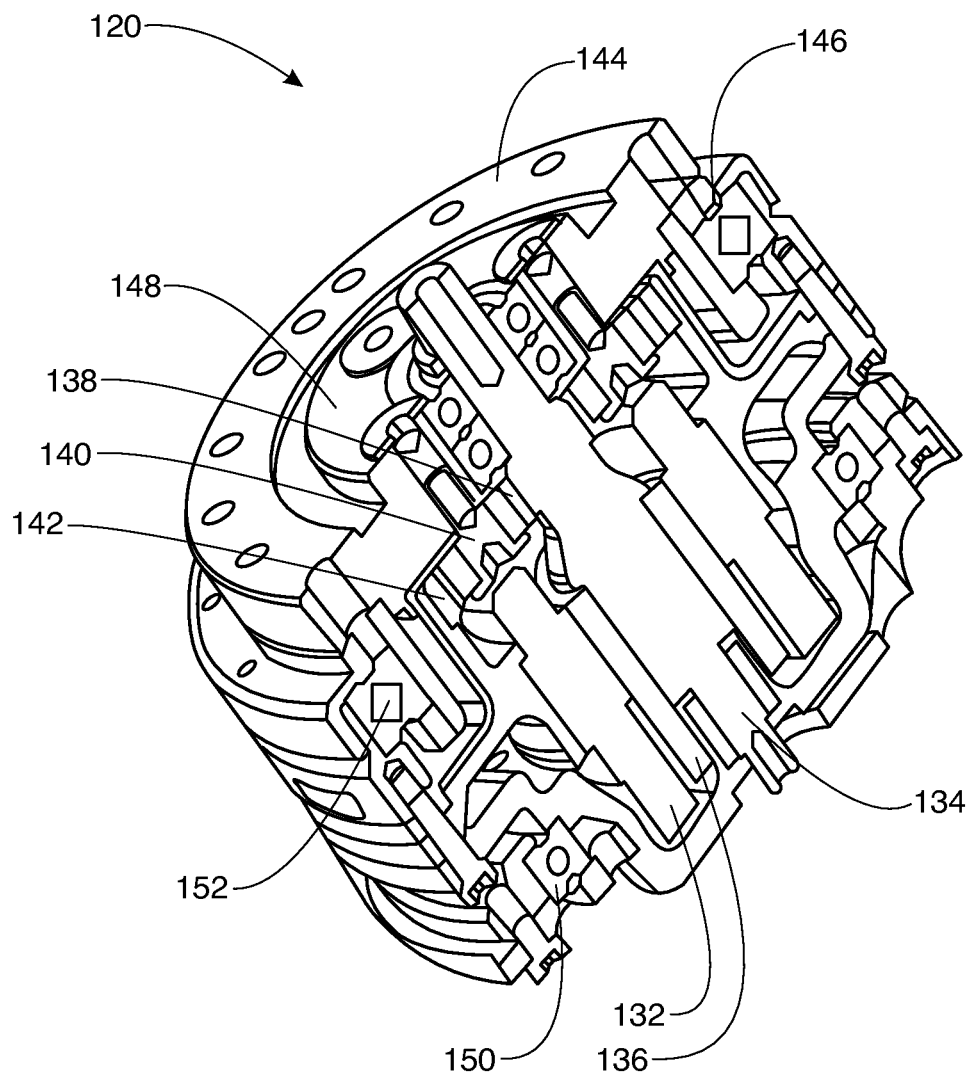
FIG. 19 is a cross-sectional perspective view of one embodiment of the elbow flexion assembly shown without the radial mount.

Referring to FIG. 19, the elbow joint 120 includes an elbow motor armature 132 that drives an elbow motor rotor 134. Elbow magnets 136 are disposed at one end of the motor rotor 134, and the opposing end of the motor rotor 134 has a sun gear 138. As the motor armature 132 drives the sun gear 138, the sun gear 138 in turn drives four planetary gears 140 positioned equidistant from each other around the sun gear 138. The four planetary gears 140 in turn react against a ring gear 142, giving the elbow flexion assembly 18 a first stage of speed reduction through an elbow harmonic drive wave generator 148 which also acts as the planet carrier. The elbow harmonic drive wave generator 148 powers the elbow harmonic drive flexspline 146, which drives against the elbow harmonic drive circular spline 144, giving the elbow flexion assembly 18 a second stage of reduction. The elbow harmonic drive flexspline 146 then drives the motion of the elbow flexion assembly 18. Bearings 150 and crossed roller bearings 152 support the outer perimeter of the elbow flexion assembly 18. Although described with both a planetary gear system and an elbow harmonic drive, the elbow flexion assembly 18 could be controlled solely by a harmonic drive by changing the gear reduction ratio.

Figure 20:
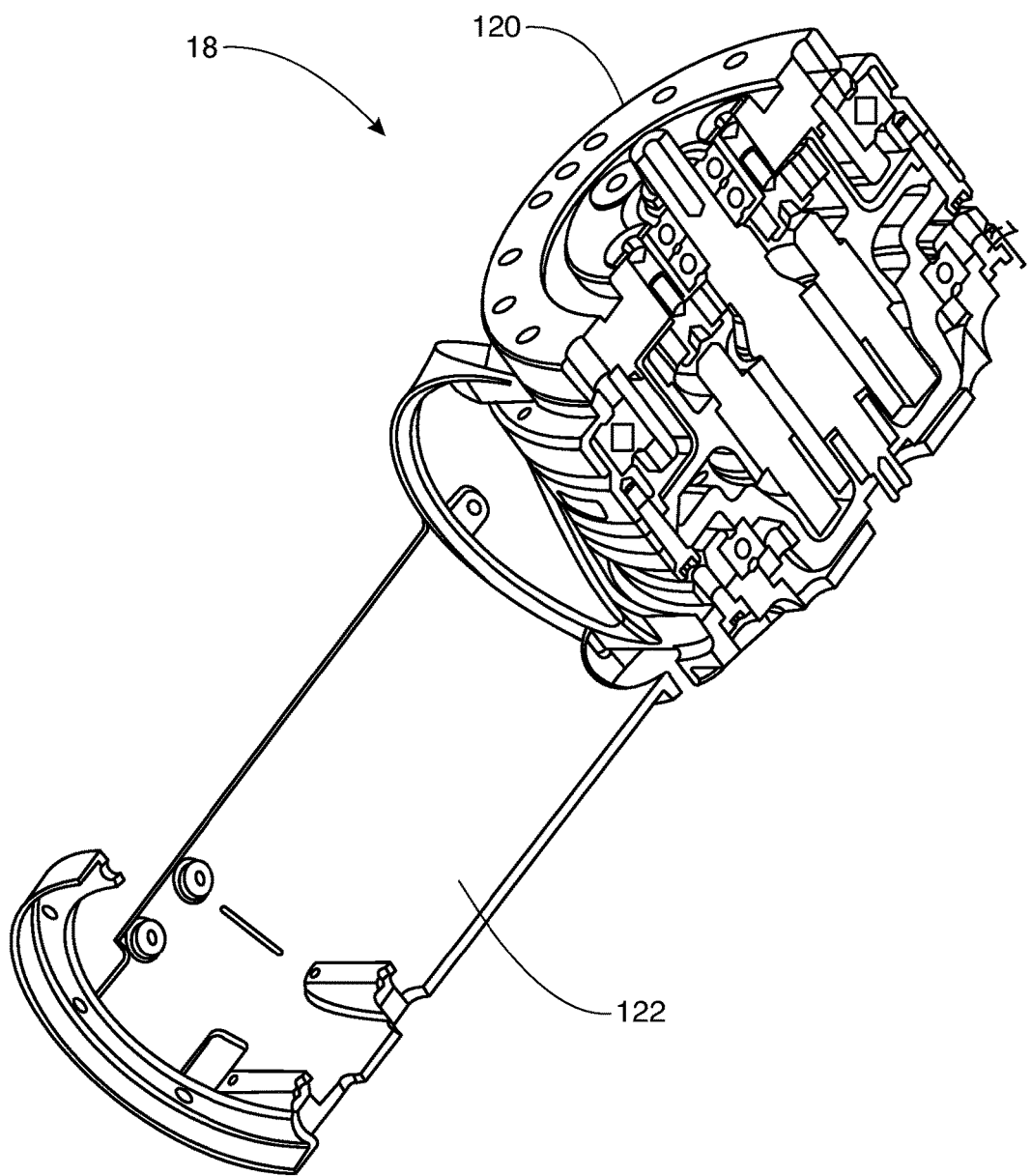
FIG. 20 is a cross-sectional perspective view of the elbow flexion assembly shown with the radial mount.
Figure 21:
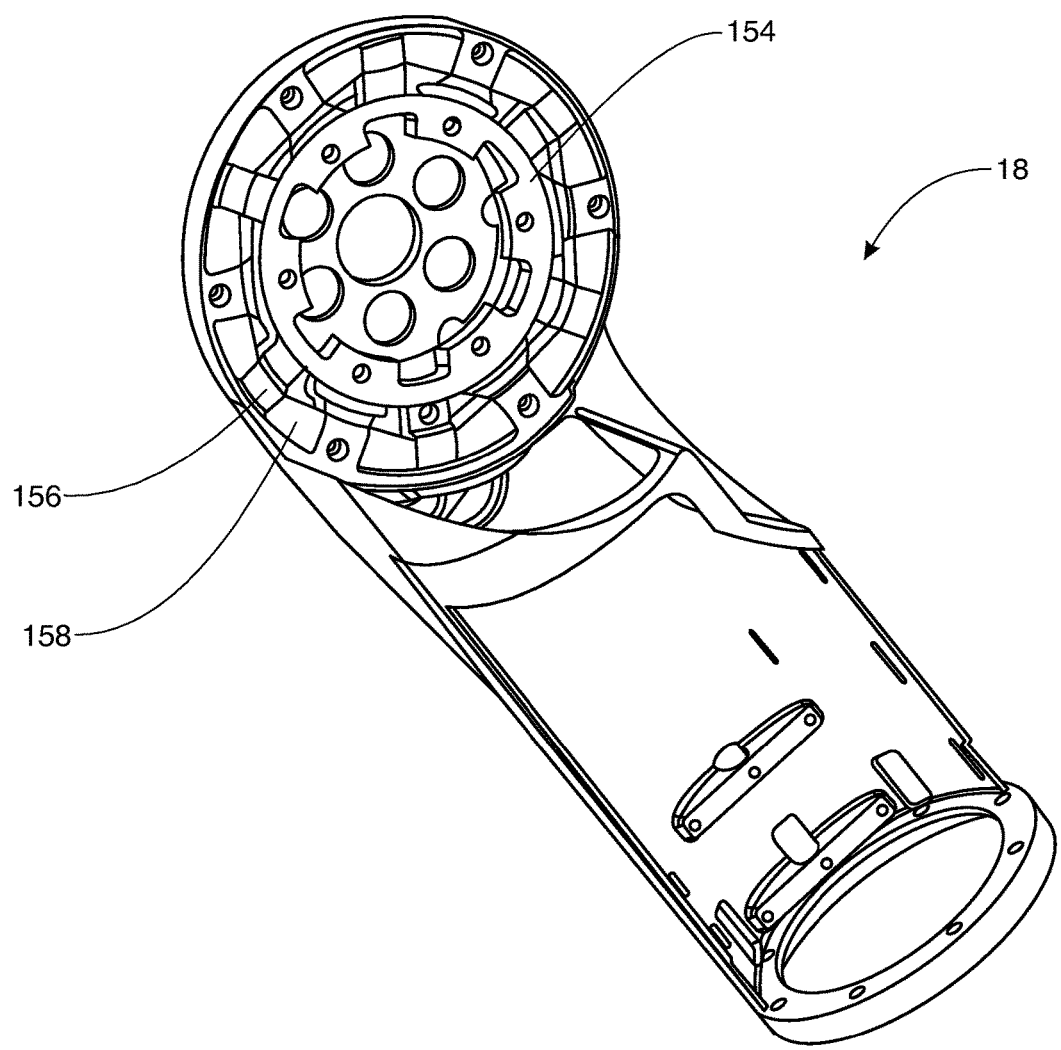
FIG. 21 is a perspective view showing the compliance subassembly of the elbow flexion assembly of FIG. 19.

Referring to FIG. 20, in the embodiment shown, the radial mount 122 is structurally fixed to the elbow joint 120, such that when the elbow joint is actuated, the radial mount 122 moves. Referring to FIG. 21, an elbow compliance subassembly 154 is incorporated into the elbow flexion assembly 18. A plurality of arms 156 extends from the center portion of the elbow compliance subassembly 154. Each arm 156 has an elbow series elastic element 158 disposed on either side of the arm 156. Similar to the shoulder flexion assembly 14, if the elbow flexion assembly 18 is subject to a torque, the elbow compliance subassembly 154, with its series elastic elements 158, is capable of absorbing the shock attenuating the torque magnitude through the rest of the elbow flexion assembly 18.

Figure 22:
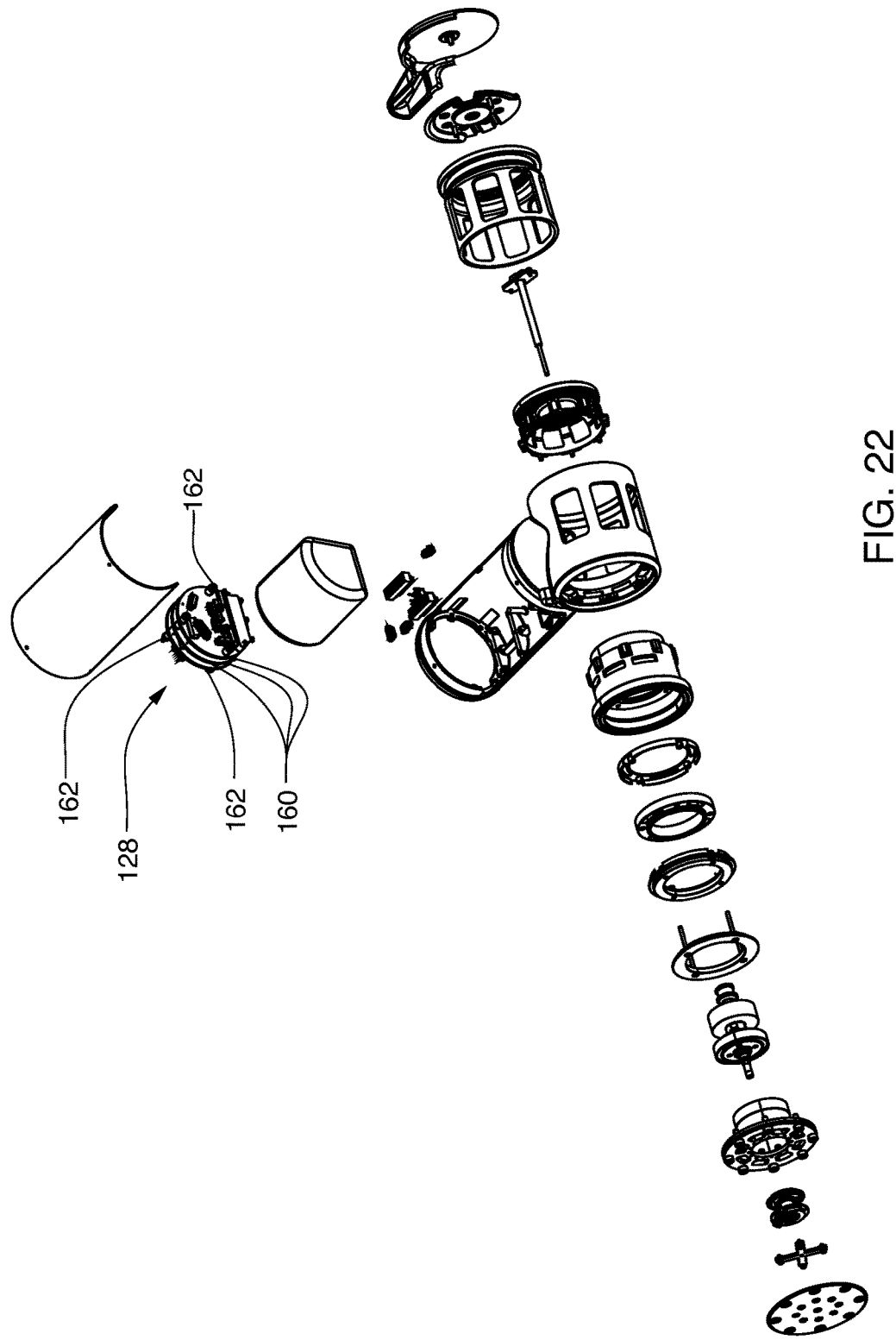
FIG. 22 is an exploded perspective view of the elbow flexion assembly of FIG. 18.

Referring to FIG. 22, the ACM stack 128, includes circuit boards 160 connected to one another by structural standoffs 162. The structural standoffs 162 are constructed of a conductive material, so that electrical power may be passed through the circuit boards 160. The structural standoffs allow power to be supplied to each circuit board 160 without conventional power connections.

Figure 23:
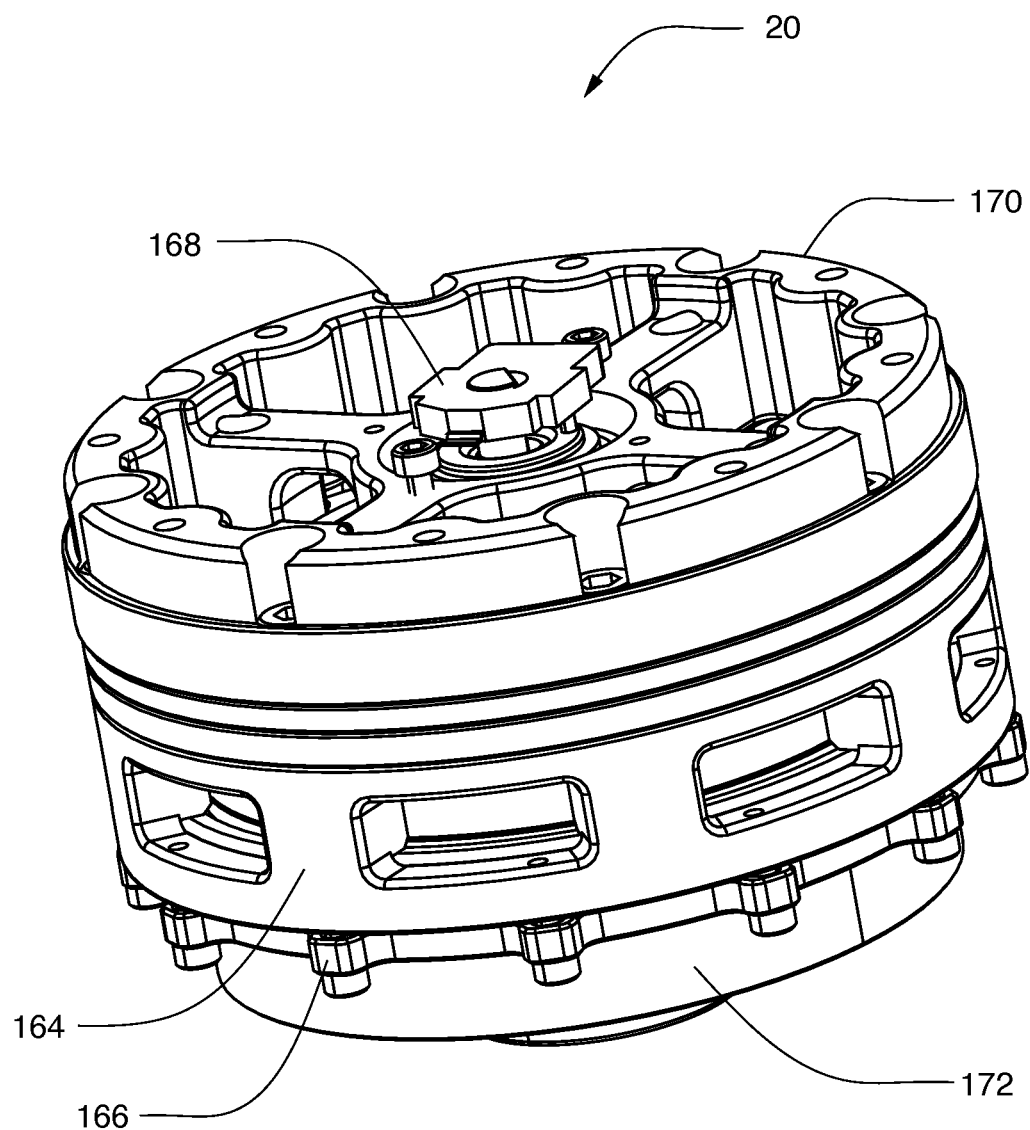
FIG. 23 is a perspective view of a wrist rotator of the prosthetic arm apparatus of FIG. 1 according to the present invention.

Referring to FIG. 23, the wrist rotator 20 includes a wrist outer bearing carrier 164, a wrist clamp 166, a wrist potentiometer 168, an elbow interface 170, and a wrist flexion assembly interface 172.

Figure 24:
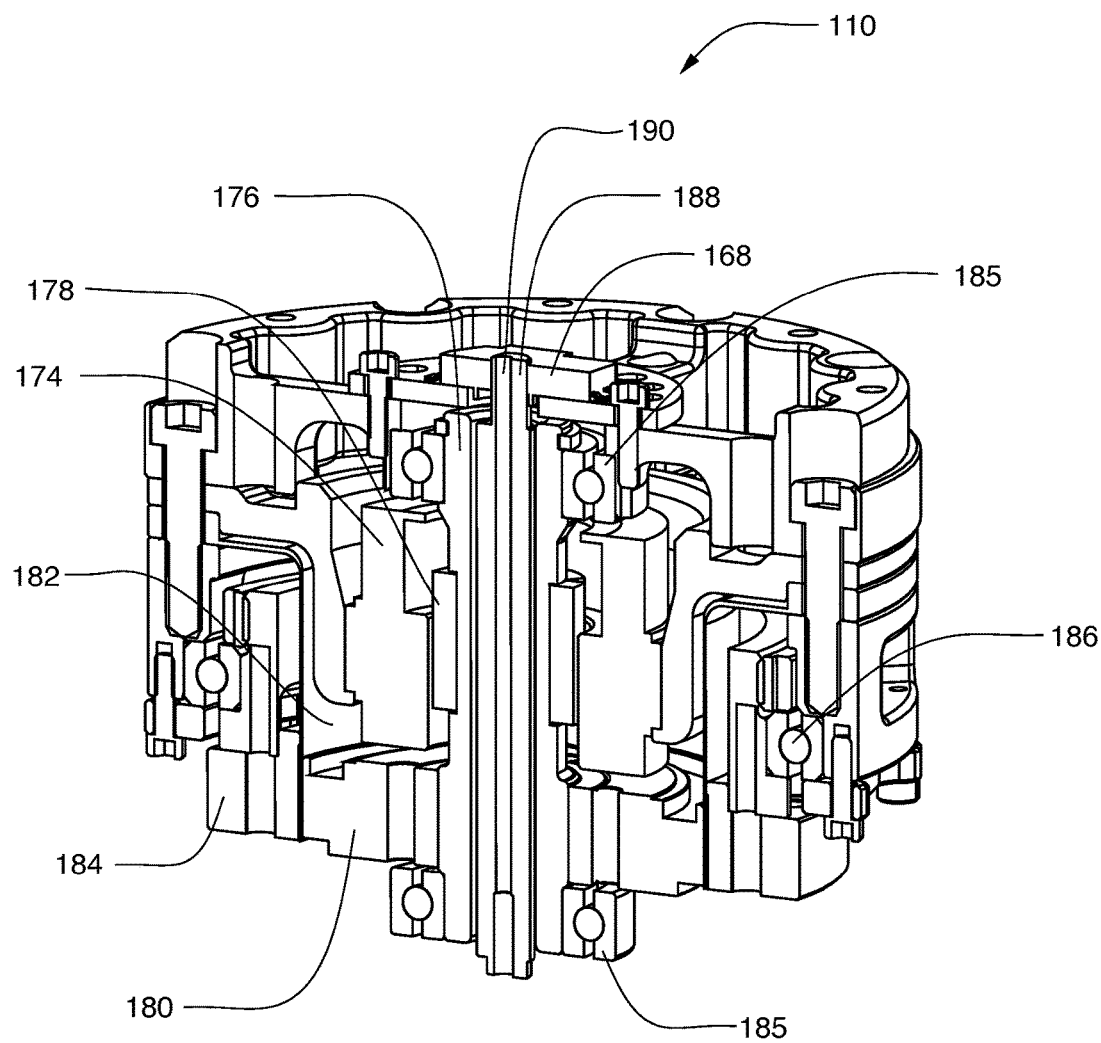
FIG. 24 is a cross-sectional perspective view of the wrist rotator of FIG. 23.

Referring to FIG. 24, movement of the wrist rotator 20 is controlled by a harmonic drive similar to that described for the humeral rotator. A wrist rotator motor armature 174 drives a wrist rotator motor rotor 176 having wrist rotator magnets 178 disposed to its surface. The lower portion of the wrist rotator motor rotor 176 integrates a wrist rotator harmonic drive wave generator 180. A wrist rotator harmonic drive flexspline 182 rotates with the wrist rotator harmonic drive wave generator 180 against a wrist rotator harmonic drive circular spline 184, resulting in reduction in the speed of rotation as the wrist rotator harmonic drive flexspline 182 causes the wrist flexion assembly interface 172 to move with respect to the rest of the wrist rotator 20. Bearings 185 support the wrist rotator motor rotor 176. Bearings 186 support the harmonic drive components 180, 182, and 184.

Still referring to FIG. 24, the wrist potentiometer 168 of the wrist rotator 20 is disposed at one end of a wrist shaft 188 and measures the rotational displacement thereof. The wrist shaft 188 may be tubular, having an electronics channel 190 for passing electronic power and controls through the wrist rotator 20.

Figure 25:
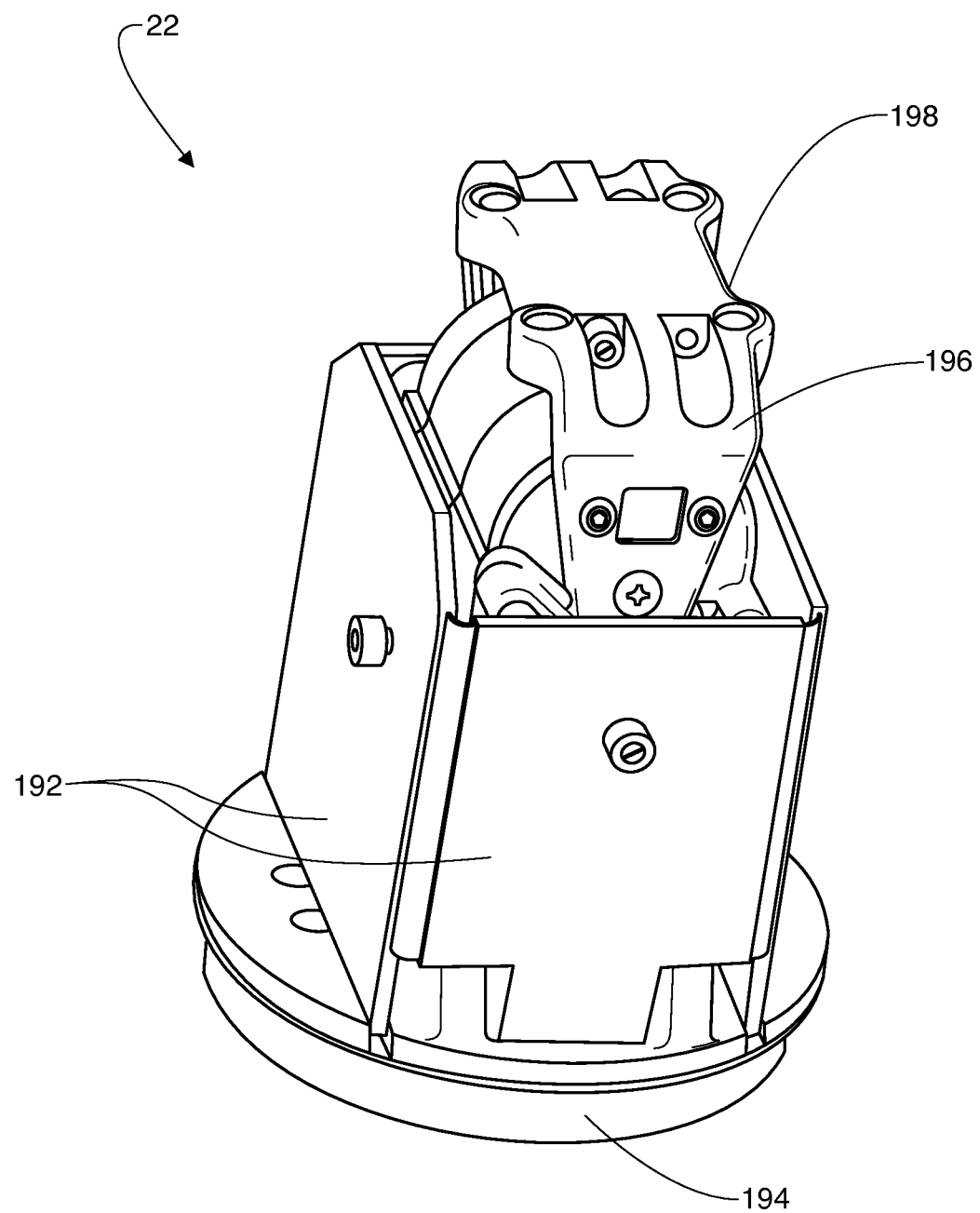
FIG. 25 is a perspective view of a wrist flexion assembly and a hand control module of the prosthetic arm apparatus of FIG. 1 according to the present invention.
Figure 26:
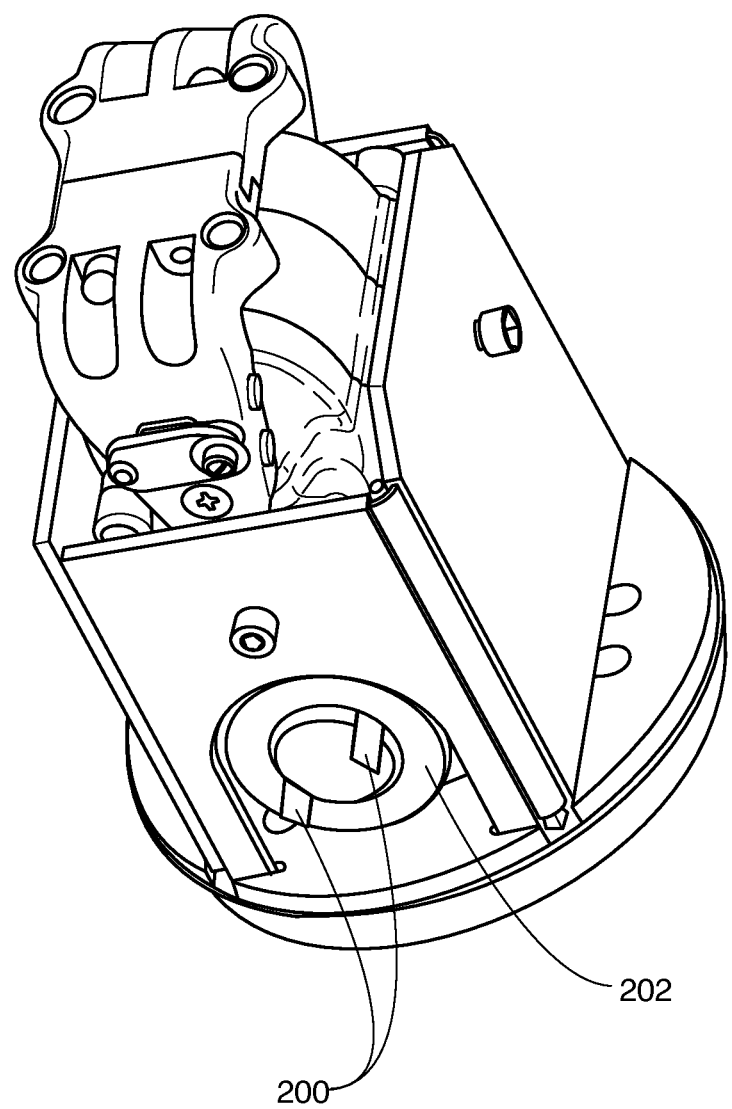
FIG. 26 is a rear perspective view of the wrist flexion assembly and hand control module of FIG. 25.

Referring to FIG. 25, the wrist flexion assembly 22 includes hand control module circuit boards 192, an input support structure 194, an output arm 196, and a hand interface 198. The input support structure 194 connects the wrist rotator 20 with the wrist flexion assembly 22. The output arm 196 has positive and negative flexion, such that the output arm 196 is able to move in two opposite directions in reference to the support structure 194. The hand interface 198 allows the hand assembly 24 to be connected to the wrist flexion assembly 22. Referring to FIG. 26, the wrist flexion assembly 22, has wrist electrical connections 200 for supplying power to a wrist flexion motor 202.

Figure 27:
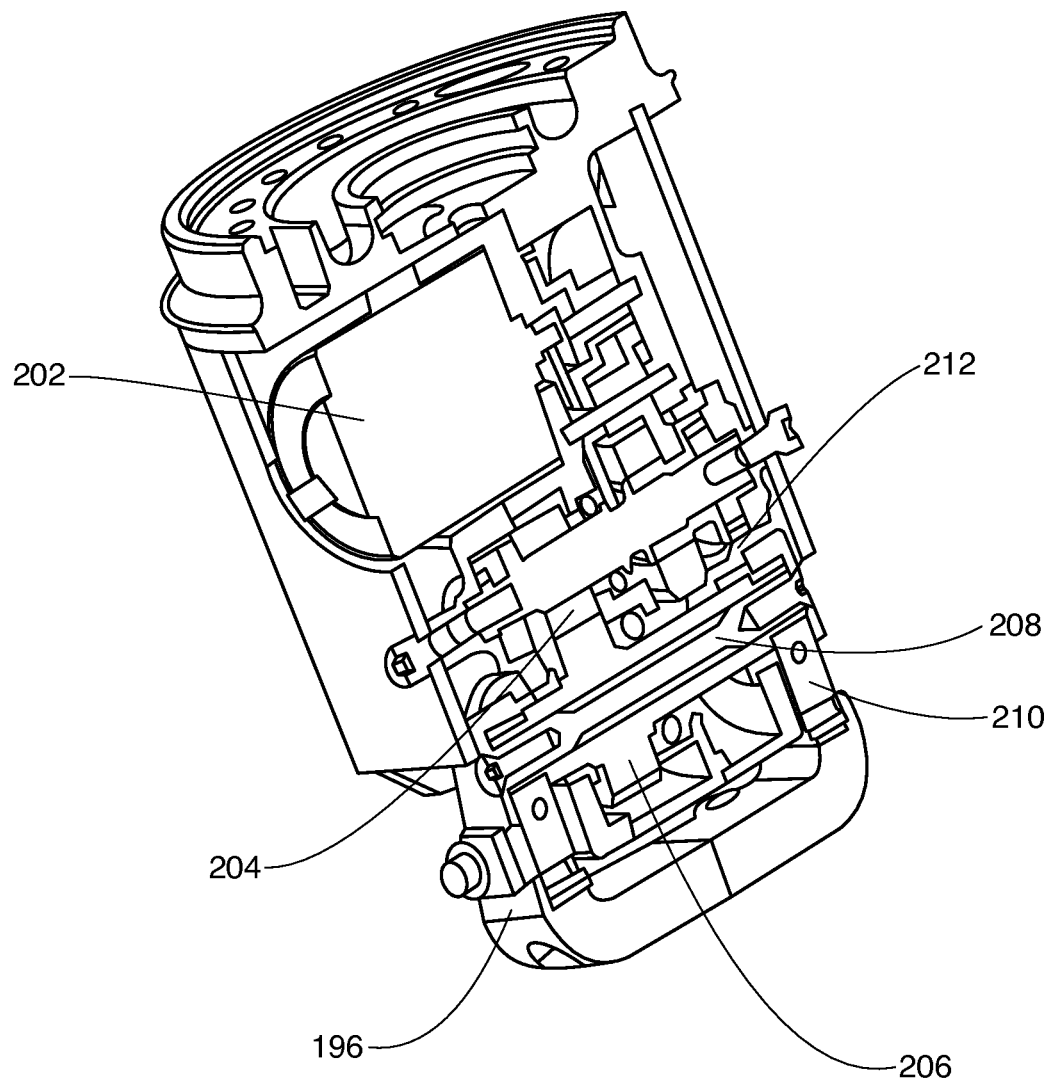
FIG. 27 is a cross-sectional perspective view of the wrist flexion assembly and hand control module of FIG. 25.

Referring to FIG. 27, in the embodiment shown, the wrist flexion motor 202 drives a wrist flexion output gear 204, which in turn drives a wrist flexion final stage-driven gear 206. A wrist flexion pivot axle 208 of the output arm 196 is axially disposed inside an opening defined by the interior of the wrist flexion final stage-driven gear 206. Wrist flexion series elastic elements 210 are disposed in the interior of the output arm 196. Movement of the wrist flexion final stage-driven gear 206 facilitates the positive and negative motion of the output arm 196. A non-backdriving clutch 212 is disposed at one end of the wrist flexion output gear 204.

Figure 28:
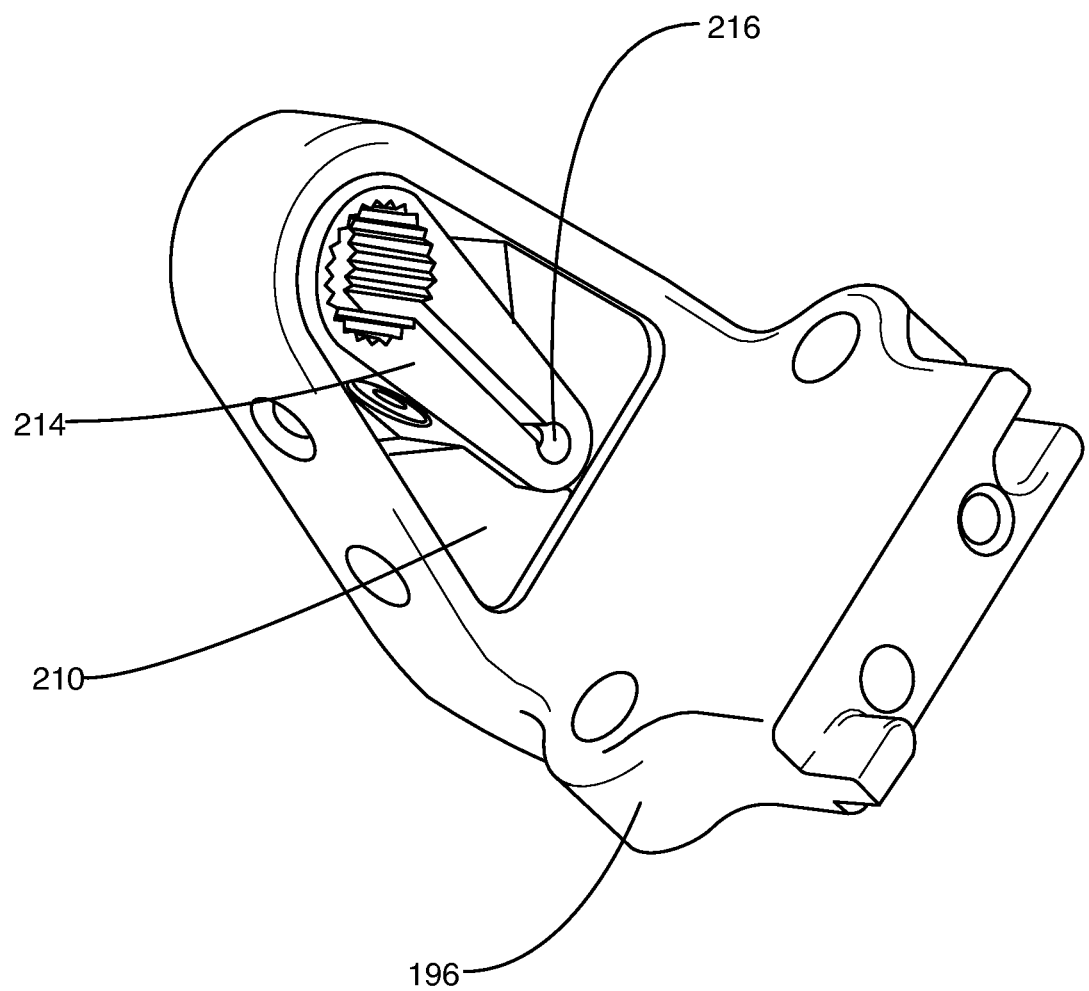
FIG. 28 is a perspective view of a wrist assembly output arm of FIG. 25.

Referring to FIG. 28, the output arm 196 has a wrist flexion drive arm 214, which is driven by the wrist flexion final stage-driven gear 206. The end of the wrist flexion drive arm 214 accommodates a wrist flexion compliance sensor magnet 216. The wrist flexion series elastic elements 210 are disposed on either side of the wrist flexion drive arm 214, and the wrist flexion series elastic elements 210 and the drive arm 214 are substantially enclosed within the output arm 196. Similar to the elbow flexion assembly 18 and the shoulder flexion assembly 14, if the wrist flexion assembly 22 is subjected to a force, the wrist flexion drive arm 214 compresses the wrist flexion series elastic elements 210 and attenuates the force through the rest of the wrist flexion assembly 22.

Figure 29:
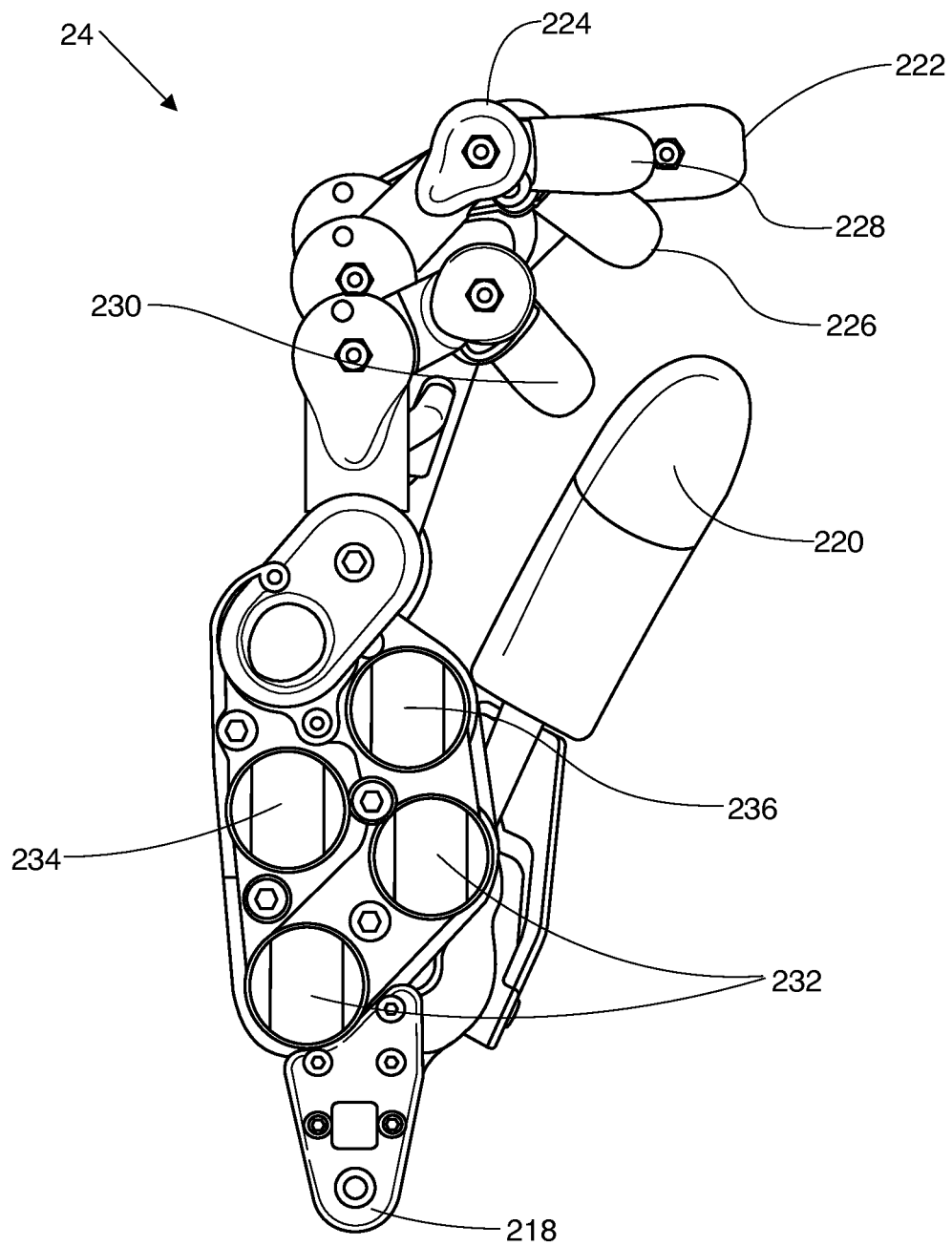
FIG. 29 is a side view of a hand assembly of the prosthetic arm apparatus of FIG. 1 according to one embodiment.
Figure 30:
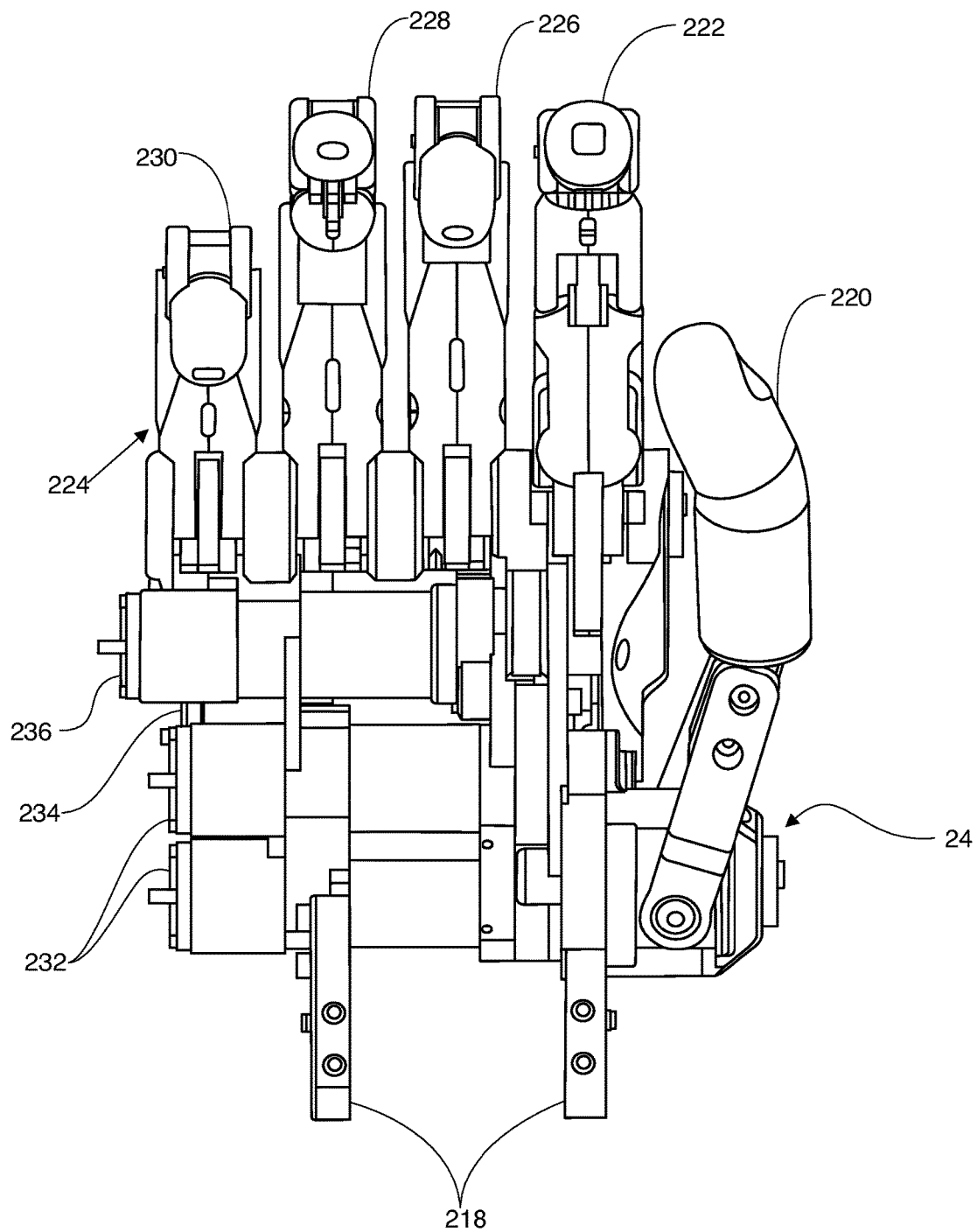
FIG. 30 is a front view of one embodiment of the hand assembly of FIG. 29.

The following is a description of one embodiment of the hand assembly. Other embodiments of the hand assembly are described and shown elsewhere in this specification. Referring to FIGS. 29 and 30 the hand assembly 24 includes a hand support 218 for providing an interface for connecting the hand assembly 24 to the wrist flexion output arm 196. The hand assembly 24 also includes a thumb structure 220, an index finger structure 222, and an MRP structure 224 replicating a middle finger 226, a ring finger 228, and a pinky finger 230. The thumb structure 220 is driven by two thumb drives 232 that feed into a single differential, giving the thumb structure 220 two degrees of freedom of movement. The index finger structure 222 is driven by a single index drive 234 and the MRP structure 224 is driven by a single MRP drive 236 that feeds a double differential.

Figure 31:
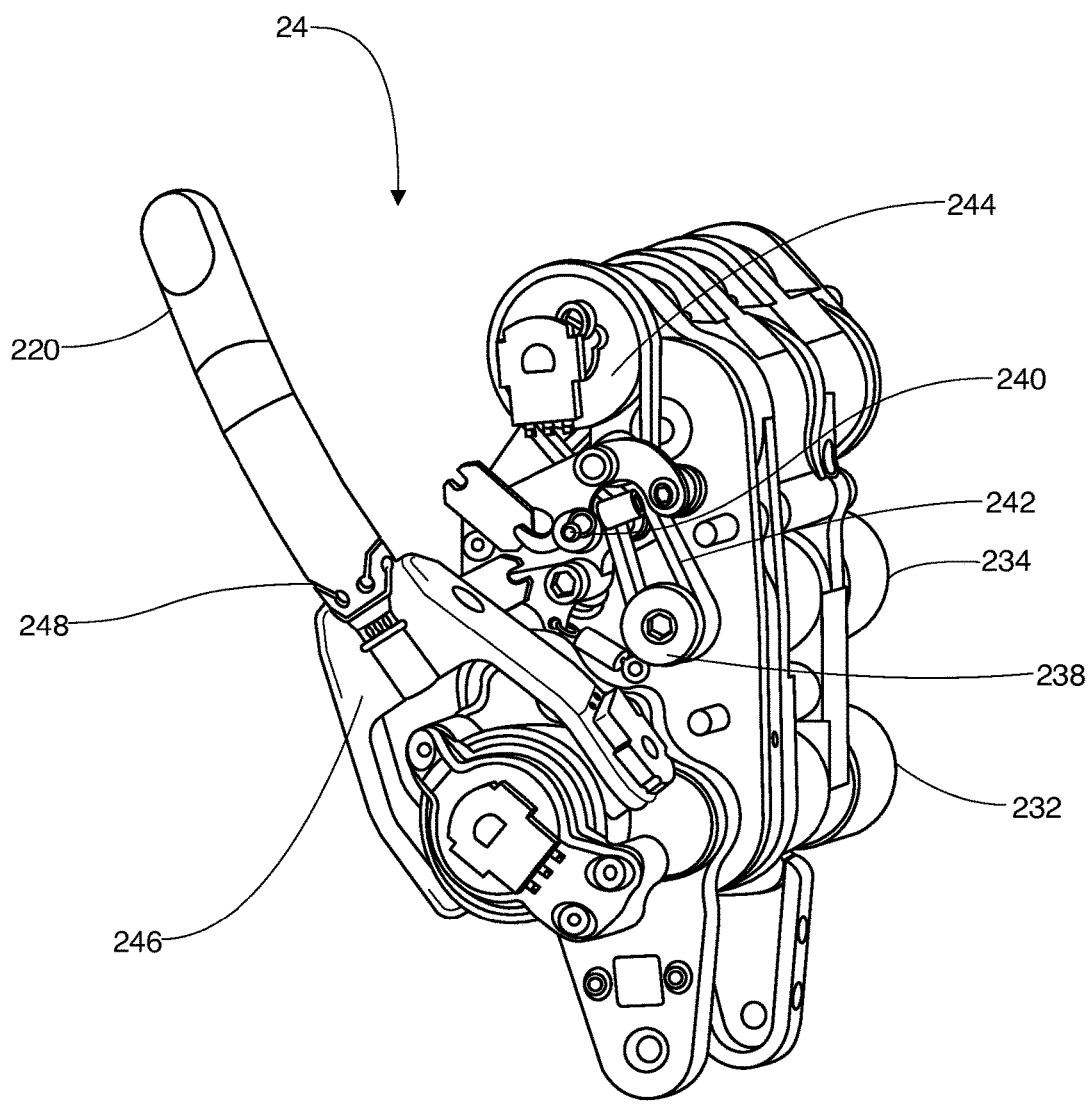
FIG. 31 is a perspective view of one embodiment of the hand assembly of FIG. 29 showing an index finger tensioner assembly.

Referring to FIG. 31, the index finger structure 222 (not shown) is driven by the index drive 234 through an index drive pulley 238, an index tensioner 240, an index tension belt 242, and an index finger pulley 244. The index drive pulley 238 is stage driven and transfers the torque to the index tension belt 242, which in turn rotates the index finger pulley 244, causing the index finger structure 222 to move. As the index tension belt 242 transfers the torque, one side of the index tension belt 242 tightens and the other side loosens, depending on which direction the index drive pulley 238 is rotated. The index tensioner 240 is located between the index drive pulley 238 and the index finger pulley 244 and the index tensioner 240 displaces in relation to the change in load to maintain the tension of the index tension belt 242. The index tensioner 240 has one side grounded and the other side capable of displacement upon the application of a load. The index tensioner 240 may instead ground the moveable side of the index tensioner 240 with a spring.

Figure 38:
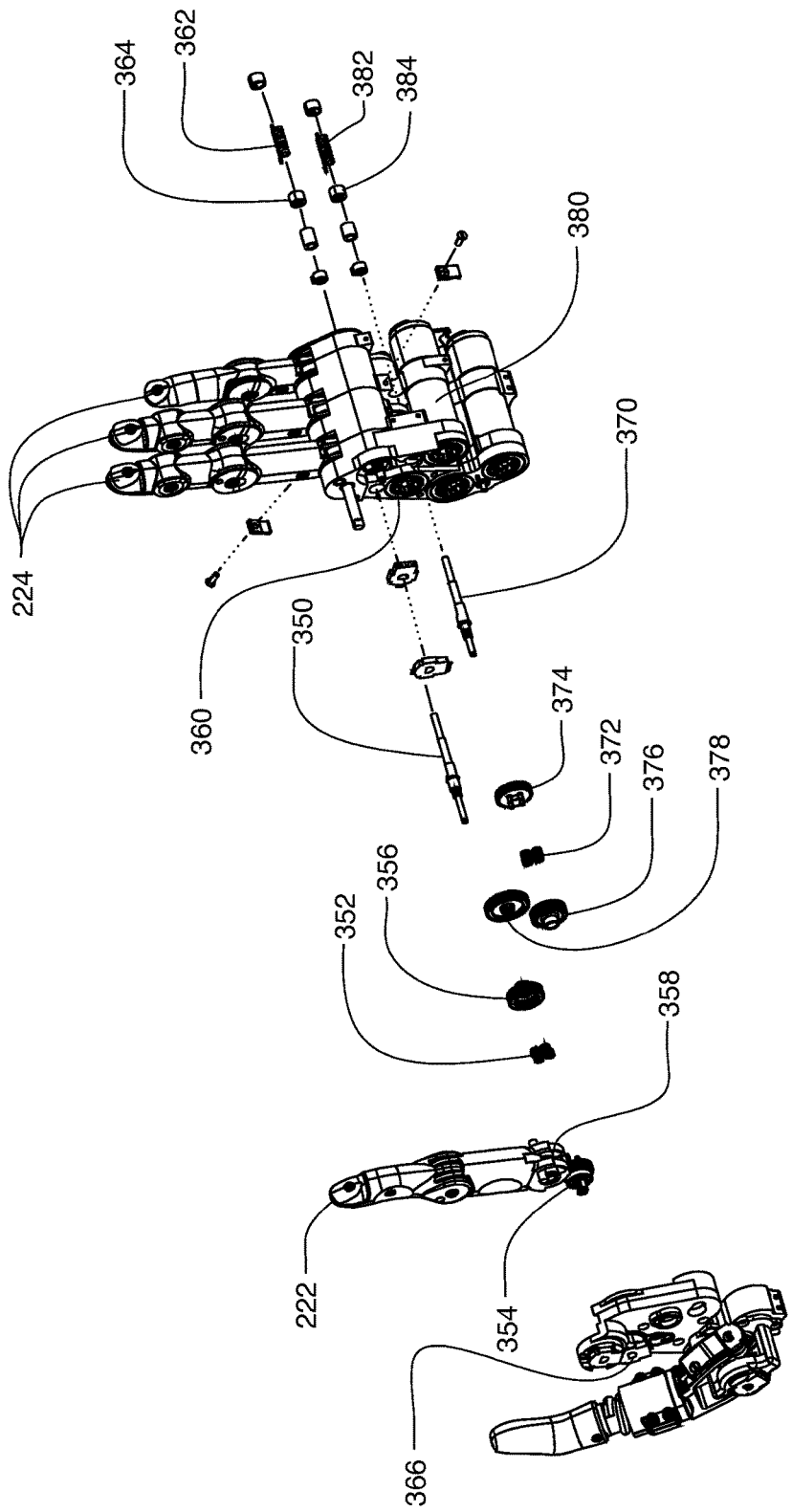
FIG. 38 is an exploded view of a portion of the hand showing another embodiment of the index and MRP fingers drives.
Figure 39:
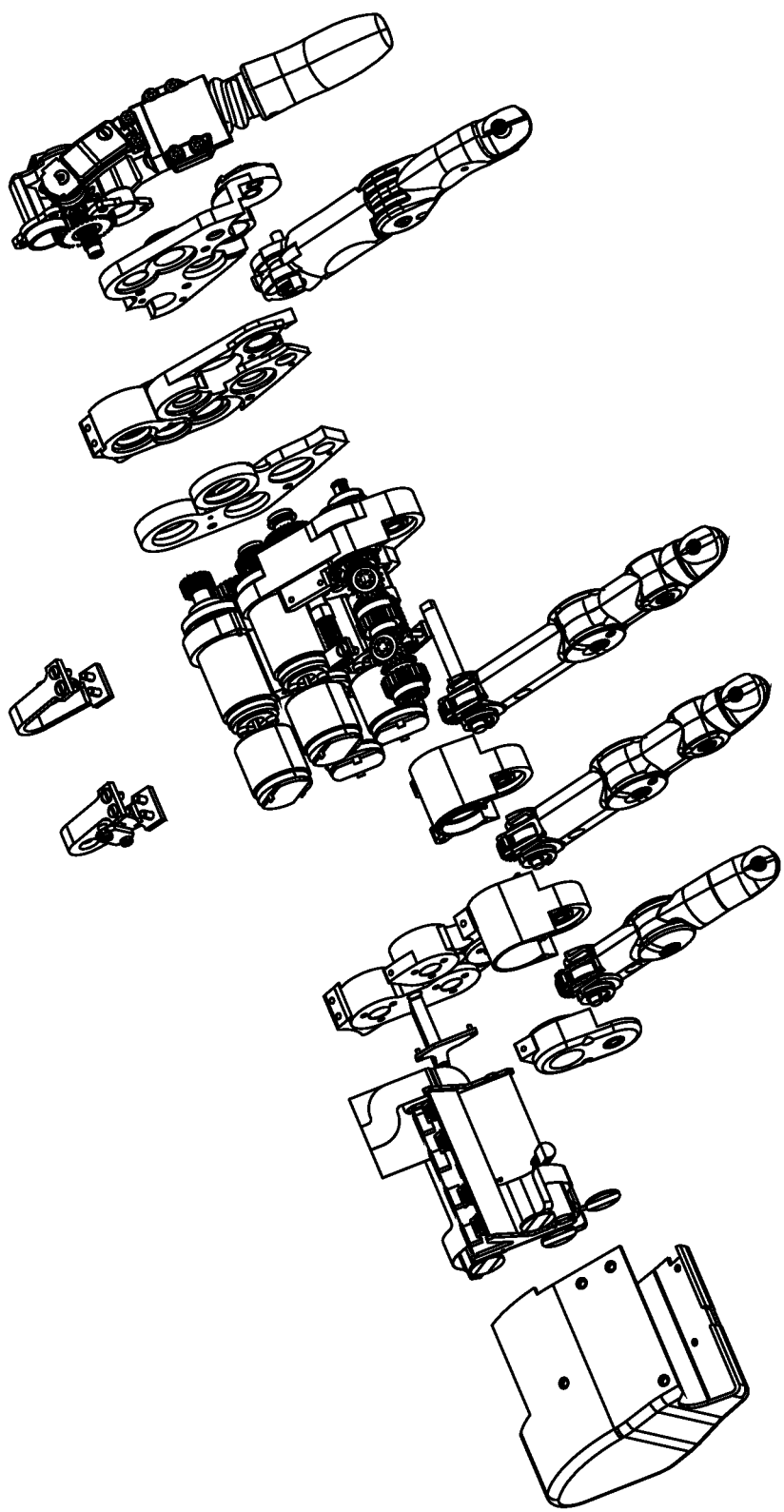
FIG. 39 is an exploded view of another embodiment of the hand.
Figure 40:
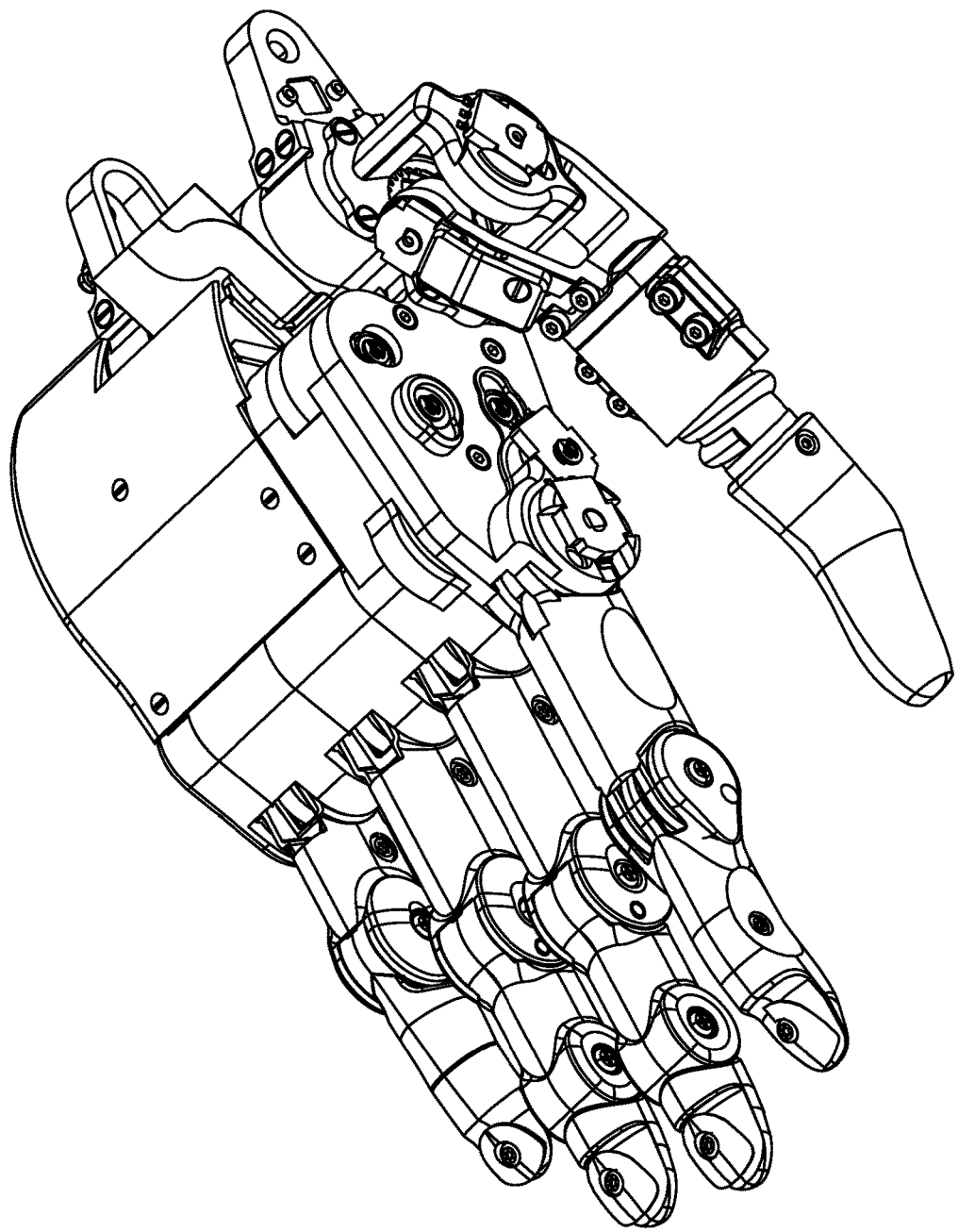
FIG. 40 is a perspective view of another embodiment of the hand.

Referring to FIG. 38, in another embodiment, the index finger structure 222 is driven through an index sun shaft 350, a set of index planets 352, an index planet carrier 354, an index ring gear 356, and an index drive gear 358. The index drive 360 drives the index ring gear 356, turning the index planets 352, the turning of which causes the index planet carrier 354 to rotate. The index drive gear 358 is driven by the external teeth of the index planet carrier 354, causing the index structure 222 to move. Any torque transmitted by the index planet carrier 354 will react against the index sun shaft 350 causing it to rotationally displace the index spring 362 through the index spring mount 364. This rotational displacement, sensed by an index potentiometer 366 can be used to infer the load on the index finger structure 222. This rotational displacement can be used to store elastic energy.

Referring to FIG. 31, the thumb structure 220 is mounted on a thumb support 246, which is driven by the two thumb differential drives 232. The thumb structure 220 has flexural cuts 248 at its base allowing the compliant thumb structure 220 to move when a load is applied to it.

Figure 32:
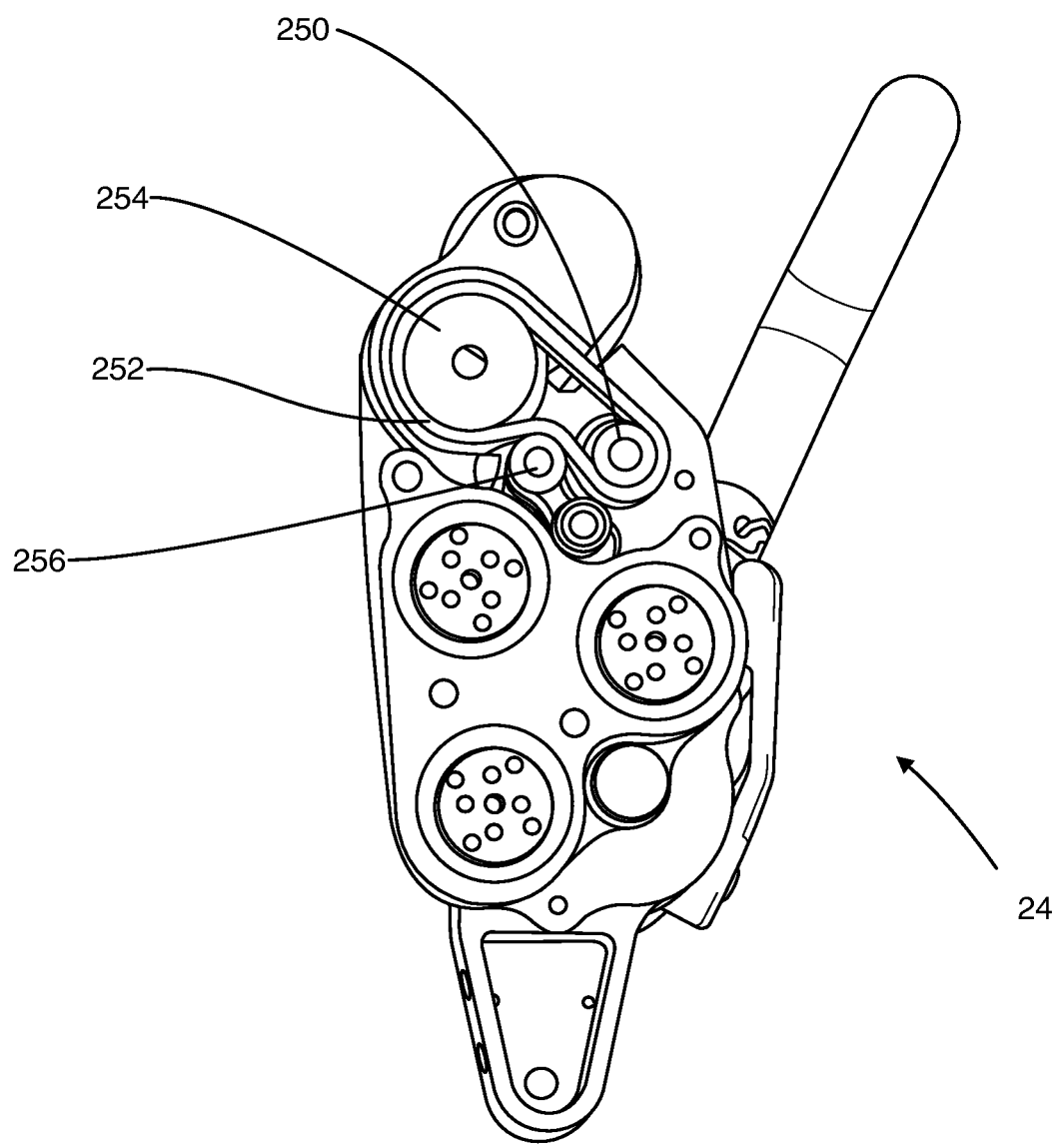
FIG. 32 is a cross-sectional view of one embodiment of the hand assembly of FIG. 29 showing an MRP tensioner assembly.

Referring to FIG. 32, the hand assembly 24 includes an MRP drive pulley 250 driven by the MRP drive 236 (not shown). The MRP drive pulley 250 is connected through an MRP tension belt 252 to the MRP pulley 254, enabling movement of the MRP structure 224. The MRP drive pulley 250 is stage driven and transfers the load to the MRP tension belt 252, which in turn rotates the linked MRP structure 224 via the MRP pulley 254. As the MRP tension belt 252 transfers the torque, one side of the MRP tension belt 252 tightens as the other side loosens. An MRP tensioner 256 located at one side of the MRP tension belt 252 displaces in relation to the change in load to maintain the tension of the MRP tension belt 252.

Referring to FIG. 38, in another embodiment, the MRP finger structures 224 are driven through an MRP sun shaft 370, a set of MRP planets 372, an MRP planet carrier 374, an MRP ring gear 376, and an MRP drive gear 378. The MRP drive 380 drives the MRP ring gear 376, turning the MRP planets 372, the turning of which causes the MRP planet carrier 374 to rotate. The MRP drive gear 378 is driven by the external teeth of the MRP planet carrier 374, causing the MRP structures 224 to move. Any torque transmitted by the MRP planet carrier 374 will react against the MRP sun shaft 370 causing it to rotationally displace the MRP spring 382 through the MRP spring mount 384. This rotational displacement can be used to store elastic energy.

Figure 33:
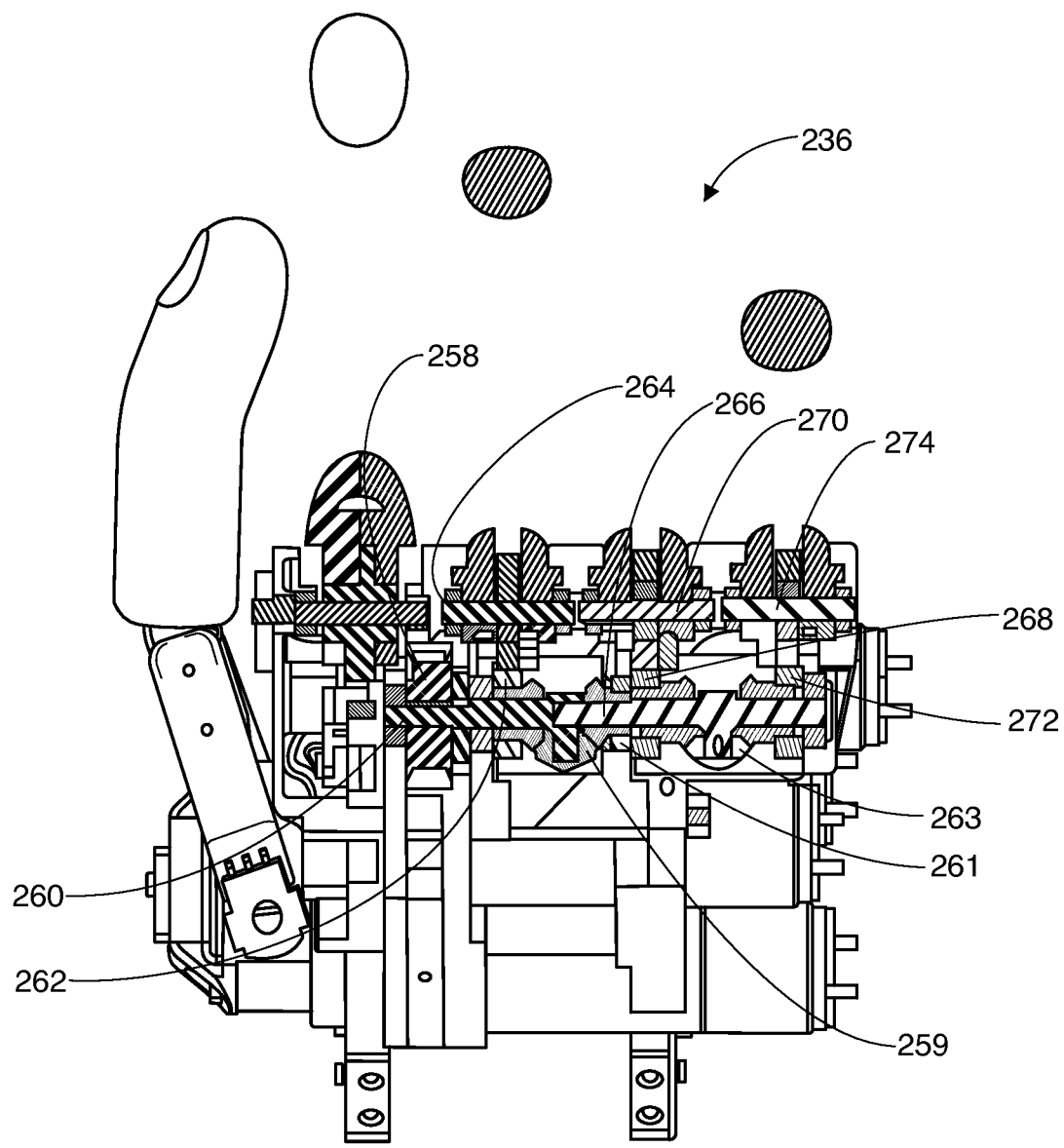
FIG. 33 is a front cross-sectional view of one embodiment of the MRP differential drive of FIG. 30.

Referring to FIG. 33 the MRP differential drive 236 includes a main MRP drive gear 258. The MRP drive gear 258 drives a first MRP input axle 260. The first MRP input axle 260 drives a first differential idler gear 259 which optionally drives a middle spur gear 262 or a differential interface gear 261. The middle spur gear 262 drives a middle pivot axle 264. The middle finger 226 is mounted on the middle pivot axle 264 and is thus actuated by the MRP differential drive 236. The differential interface gear 261 drives a second MRP input axle 266. The second MRP input axle 266 drives a second differential idler gear 263 which optionally drives a ring spur gear 268 or a pinky spur gear 272. The ring spur gear 268 drives a ring pivot axle 270. The ring finger 228 is mounted on the ring pivot axle 270 and is thus actuated by the MRP differential drive 236. The pinky spur gear 272 drives a pinky pivot axle 274. The pinky finger 230 is mounted on the pinky pivot axle 274 and is thus actuated by the MRP drive 236. While the MRP drive 236 drives the middle finger 226, the ring finger 228 and the pinky finger 230, the gear configuration of the first input axle 260 and the second input axle 266 allows independent movement for the under-actuated finger gear system of the MRP structures 224.

Figure 41:
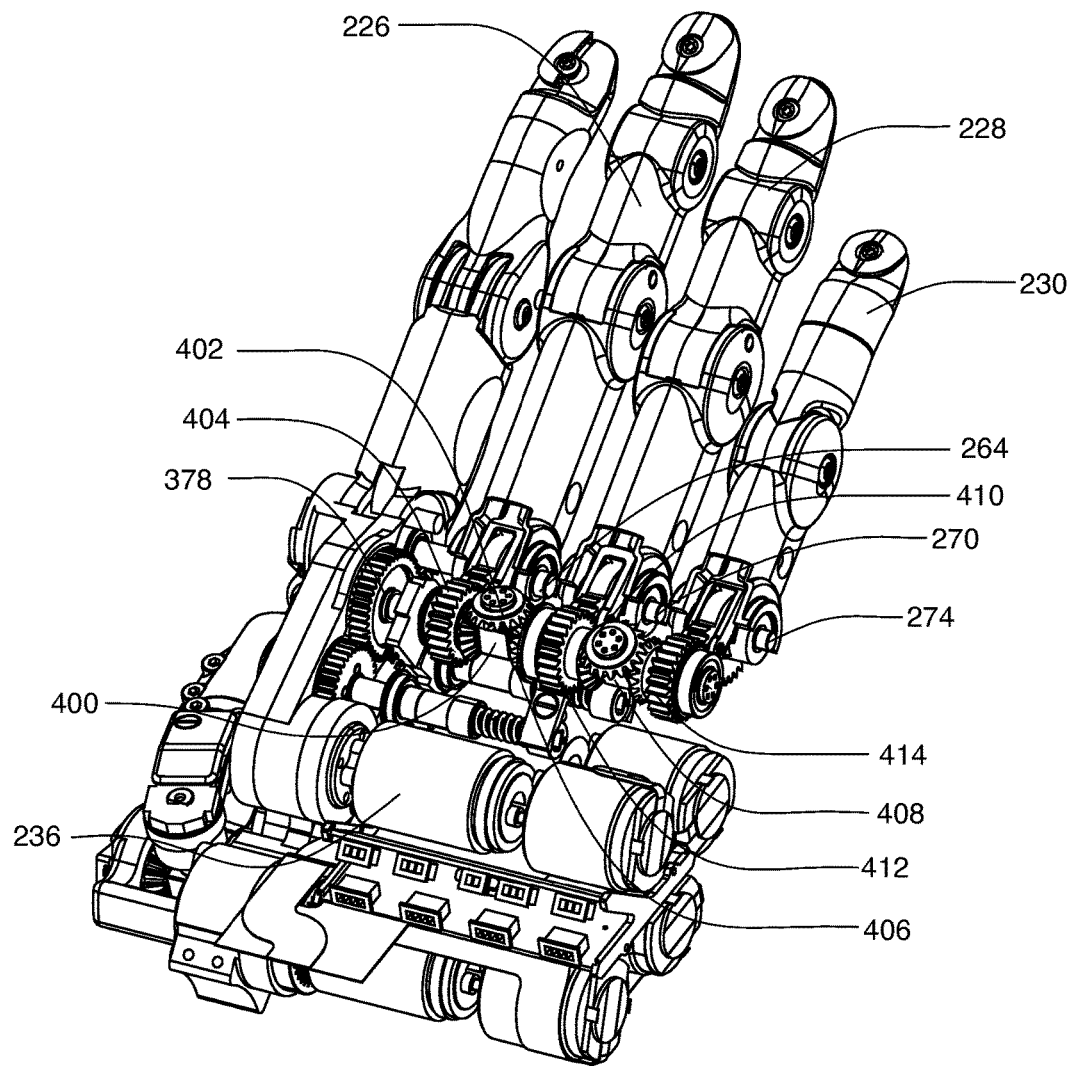
FIG. 41 is a perspective cutaway view of the hand.

Referring to FIG. 41, in another embodiment of the hand, the MRP differential drive includes an MRP drive gear 378 which drives a double differential allowing the MRP fingers to conformably wrap around an object. The MRP drive gear 378 drives a first MRP input axle 400. The first input axle 400 drives a first differential idler gear 402 which optionally drives a middle spur gear 404 or a differential interface gear 406. The middle spur gear 404 drives a middle pivot axle 264. The middle finger 226 is mounted on the middle pivot axle 264 and is thus actuated by the MRP drive 236. The differential interface gear 406 drives a second MRP input axle 408. The second MRP input axle 408 drives a second differential idler gear 410 which optionally drives a ring spur gear 412 or a pinky spur gear 414. The ring spur gear 412 drives a ring pivot axle 270. The ring finger 228 is mounted on the ring pivot axle 270 and is thus actuated by the MRP drive 236. The pinky spur gear 414 drives a pinky pivot axle 274. The pinky finger 230 is mounted on the pinky pivot axle 274 and is thus actuated by the MRP drive 236. While the MRP drive 236 drives the middle finger 226, the ring finger 228 and the pinky finger 230, the gear configuration of the first input axle 400 and the second input axle 408 allows independent movement for the under-actuated finger gear system of the MRP structures 224.

Figure 34:
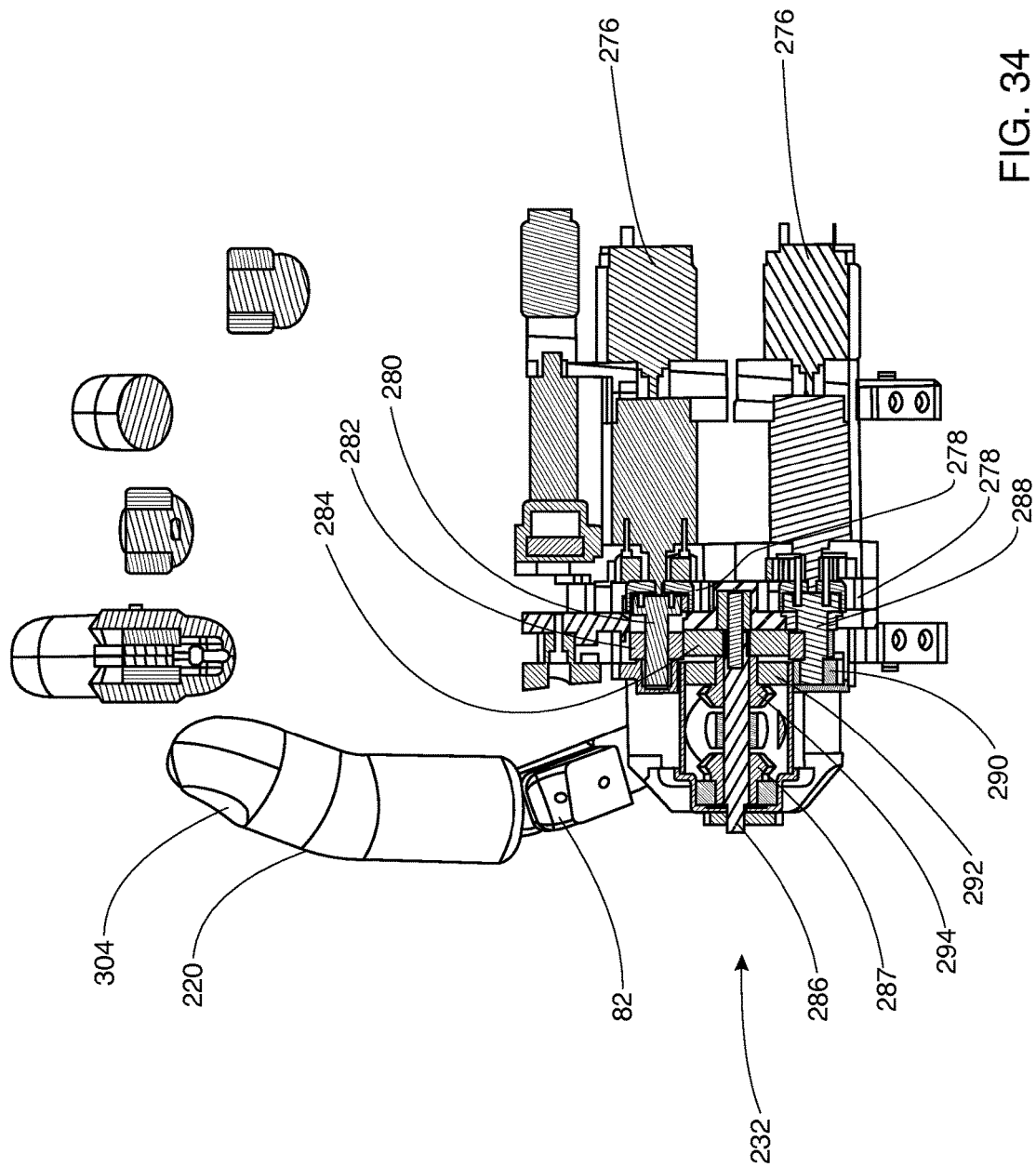
FIG. 34 is a front cross-sectional view of one embodiment of thumb differential drives and an index finger differential drive of FIG. 30.

Referring to FIG. 34 the thumb differential drives 232 control the movement of the thumb structure 220 and are driven by thumb actuators 276. The thumb actuators 276 have non-backdriving thumb clutches 278 to prevent output loads from reaching and backdriving the thumb actuators. One thumb actuator 276 drives a first thumb output drive 280 and a first thumb output gear 282. The first thumb output gear 282 in turn drives a first thumb transfer gear 284, which drives a fixed differential shaft 286. The fixed differential shaft 286 drives one thumb differential bevel gear 287. The second thumb actuator 276 drives a second thumb output drive 288 and a second thumb output gear 290. The second thumb output gear 290 drives a second thumb transfer gear 292, which drives a thumb differential bevel gear 294. The two thumb differential bevel gears 287 and 294 operate the thumb structure 220 in its two degrees of motion.

The thumb structure 220, the index finger structure 222, and MRP structure 224 in one embodiment are covered in silicone, which provides additional friction and aids in gripping objects. In some embodiments, the entire hand assembly 24 may also be covered in silicone to provide additional grip for holding objects. In other embodiments, the silicone material may be replaced by other compliant materials.

The various parts of the prosthetic arm apparatus 10 are preferably constructed from plastic or magnesium. However, where more strength is desired, the parts may be made of aluminum, titanium or steel. In other embodiments, the various parts of the prosthetic arm may be constructed of other metals or plastics, depending on the desired characteristics, including strength and weight, of the various part.

Figure 35:
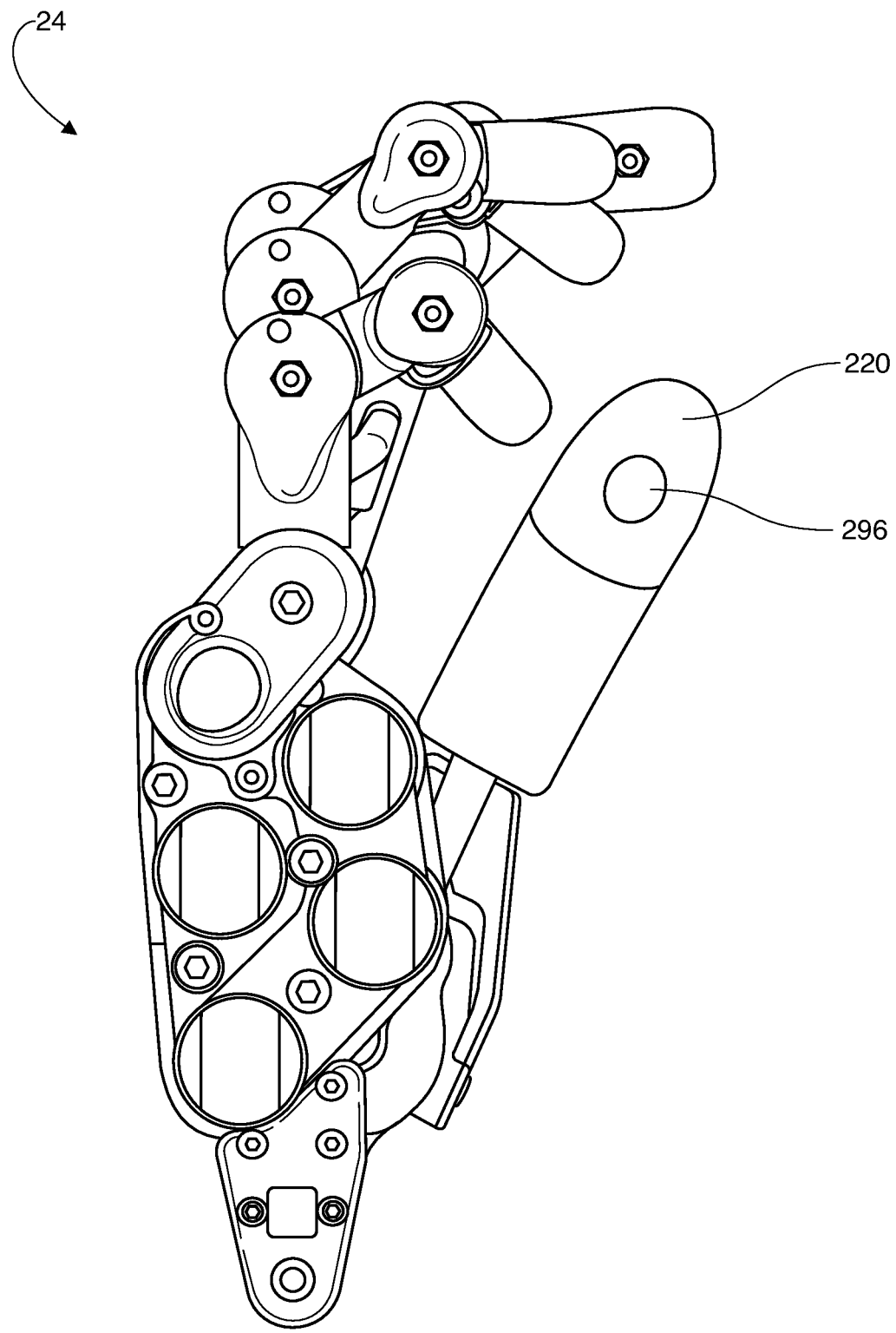
FIG. 35 is a side view of one embodiment of the hand assembly of FIG. 30 showing a tactile feedback sensor according to the present invention.
Figure 36:
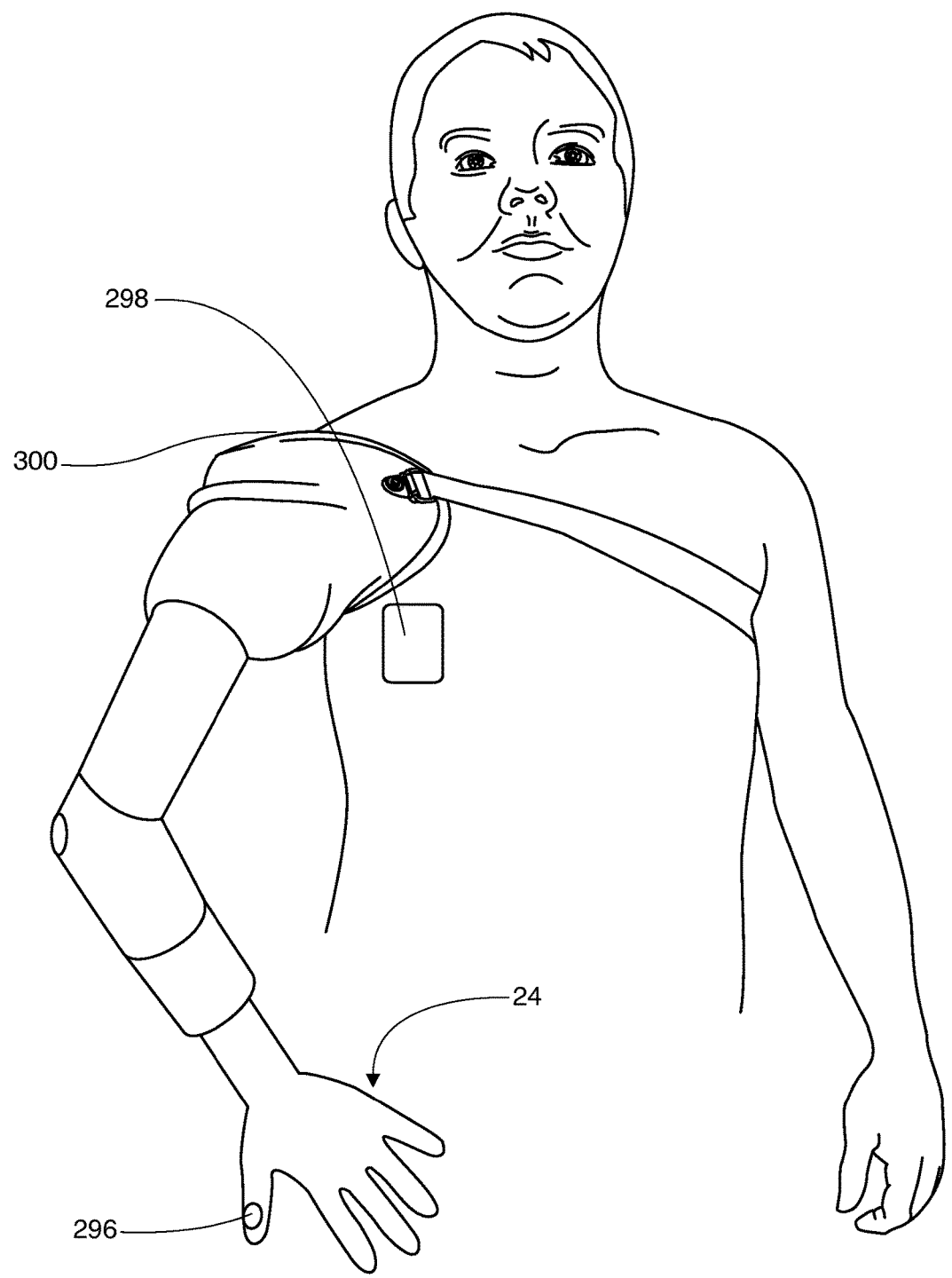
FIG. 36 is a perspective view of one embodiment of the tactile feedback sensor and a feedback actuator of the prosthetic arm apparatus of FIG. 1.
Figure 37:
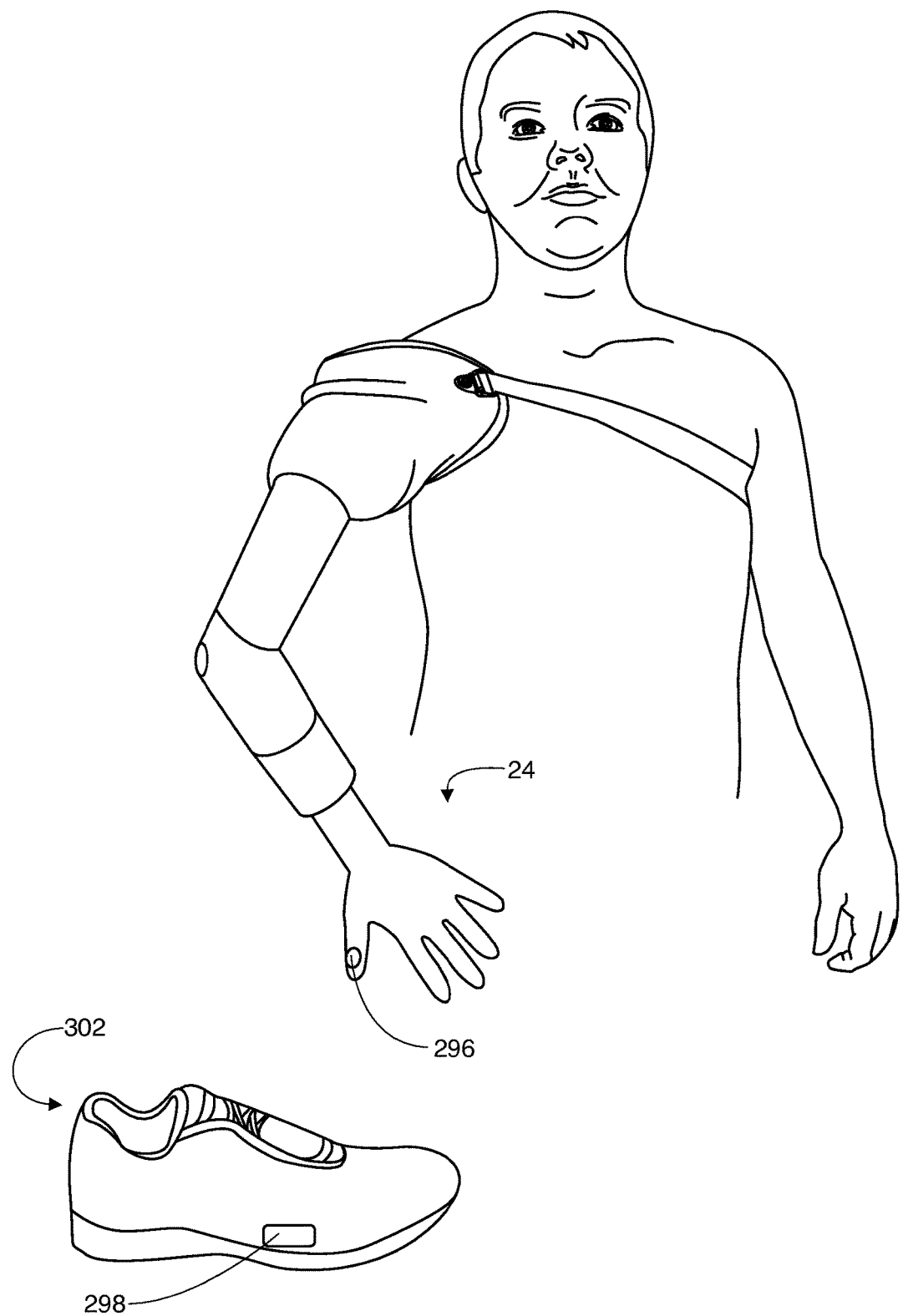
FIG. 37 is a perspective view of another embodiment of the tactile feedback sensor and feedback actuator of the prosthetic arm apparatus of FIG. 1 according to the present invention.

Referring to FIG. 35, a tactile feedback sensor 296 may be positioned on the inner side of the thumb structure 220. The tactile feedback sensor 296 may be a pressure sensor, force sensor, a displacement sensor, or other similar sensor capable of providing the user with feedback. Referring to FIG. 36, the tactile feedback sensor 296 is operatively connected to a feedback actuator 298. The tactile feedback sensor 296 may be connected to the feedback actuator 298 by either wires or wirelessly. In operation, as the user grips an object with the hand assembly 24, feedback sensor 296 reads the displacement of or the force exerted on the thumb structure 220. That reading is then sent to the feedback actuator 298, which gives the user tactile feedback that indicates the strength of the grip. Feedback actuator 298 may be placed on the chest of the user, or in any other location capable of receiving tactile feedback, such as on a user's residuum 300. Referring to FIG. 37, the feedback actuator 298 may be located on a foot controller 302 that is used to control hand assembly 24.

Feedback actuator 298 may be a vibration motor, such as any vibration motor known in the art, placed against the skin of the user. As the user grips an object, feedback actuator 298 begins vibrating, notifying the user how strong the object is being gripped. As the force on or displacement of the tactile feedback sensor 296 changes, frequency and/or amplitude of vibration may also change, notifying the amputee of a changing grip. For example, if a vibrating actuator 298 is placed at the chest of the user as in FIG. 36, the user will feel the vibration at his chest.

The feedback actuator 298 may also be placed wherever the controller for the hand assembly 24 is located. For example, if a foot controller 302 controls the hand assembly 24, the feedback actuator 298 may be incorporated into the foot controller 302. The user will then receive tactile feedback of the strength of the prosthetic grip at the same location where the controller is located.

The actuator 298 may also be a pressure actuator that applies pressure against the user's skin. For example, the actuator 298 may have a rod that increases pressure against the amputee's skin as the hand assembly 24 increases its grip on an object.

Although described with a single tactile feedback sensor 296, additional tactile feedback sensors may be placed at other locations on the hand assembly 24. For example, additional tactile feedback sensors 296 may be placed on the index finger structure 222, the MRP structures 224, on the palm of the hand assembly 24, or on any combination of these positions or any other location. Each tactile feedback sensor 296 would then be operatively connected to an associated feedback actuator 298. Multiple tactile feedback sensors 296 and actuators 298 would provide more sophisticated tactile feedback of the strength of the grip, improving the control of the hand assembly 24.

In operation, the prosthetic arm apparatus is able to move substantially similar to a human arm. Referring to FIGS. 29 and 30, starting with the hand assembly 24, the thumb structure 220, index finger structure 222, and MRP structure 224 are each driven independent of the others, and therefore, each may be actuated without actuating the other two structures. The thumb actuator 276 driving the thumb miter gear 294 controls the thumb structure's movement in a direction toward or away from the center of the palm of the hand assembly 24, as shown in FIG. 34. The thumb actuator 276 driving the lateral rotation shaft 286 controls the thumb structure's movement in a direction toward or away from the side of the palm of the hand assembly 24, as shown in FIG. 34. The thumb actuators 276 (FIG. 34) provide the thumb structure 220 with four degrees of freedom in the thumb structure's movement. The index finger structure 222, driven by a single index differential drive 234, may be actuated with two degrees of freedom. Specifically, the index finger structure 222 may be actuated toward or away from the palm of the hand assembly 24, wherein the movement path is similar to that of a human index finger while making or releasing a fist. The middle finger 226, ring finger 228, and pinky finger 230 of the MRP structure 224 are actuated by the MRP differential drive 236. Additionally, the middle finger 226, ring finger 228, and pinky finger 230 are actuated toward or away from the palm of the hand assembly 24, similar to the index finger structure 222. However, the middle finger 226, ring finger 228, and pinky finger 230 are each geared separately, such that the rate of movement of each is different, simulating human finger movement.

Referring to FIG. 1, the hand assembly 24 is mounted on the wrist flexion assembly 22 via the hand interface 198, as shown in FIG. 25. Referring to FIG. 25, as the output arm 196 of the wrist flexion assembly 22 is actuated, the hand assembly 24 is also caused to move. The output arm 196 of the wrist flexion assembly 22 may be actuated pivotally about wrist flexion pivot axle 208, as shown in FIG. 27, moving the hand interface 198 to the left or right, and thus pivoting the hand assembly 24 in relation to the input support structure 192.

Referring back to FIG. 1, the wrist flexion assembly 22 is attached to the wrist rotator 20 via wrist flexion assembly interface 172, shown in FIG. 23. Referring to FIGS. 23 and 24, when actuated, the wrist flexion assembly interface 172 is rotated about wrist shaft 188 in relation to the wrist outer bearing carrier 164. Therefore, the wrist flexion assembly 22, and attached hand assembly 24 are also caused to rotate in reference to the wrist outer bearing carrier 164 by actuation of the wrist rotator 20. Therefore, the wrist rotator 20 allows the prosthetic arm apparatus 10 to move in a way similar to a human arm opening a door.

Referring back to FIG. 1, the wrist rotator 20 is attached to the elbow flexion assembly 18 via the wrist interface 130, shown in FIG. 18. Referring to FIG. 20, when the elbow flexion assembly 18 is actuated, the radial mount 122 is rotated about the axis of motor rotor 134. The wrist rotator 20, wrist flexion assembly 22, and hand assembly 24 are thus also caused to rotate about the axis of motor rotor 134 because they are attached at the wrist interface to the radial mount 122. Therefore, the elbow flexion joint 18 allows the prosthetic arm apparatus 10 to perform hammering motion.

Referring back to FIG. 1, the elbow flexion assembly 18 is attached to the humeral rotator 16 via the humeral mount 96, shown in FIG. 27. Referring to FIG. 16, actuation of the humeral rotator 16 causes the humeral mount 96 to rotate in relation to the outer bearing carrier 90 of the humeral rotator 16. Since the elbow flexion assembly 18, wrist rotator 20, wrist flexion assembly 22, and hand assembly 24 are attached to the humeral mount 96, they are also caused to rotate in relation to the outer bearing carrier 90. This allows the prosthetic arm apparatus 10 to rotate to perform an arm wrestling motion.

Referring back to FIG. 1, the humeral rotator 16 is attached to the shoulder flexion assembly 14 though the humeral interface 46, shown in FIG. 9. Referring to FIG. 9, actuation of the shoulder flexion assembly 14 causes the main shoulder housing 42 to pivot about the center of the abductor interface 44. Since the humeral rotator 16, elbow flexion assembly 18, wrist rotator 20, wrist flexion assembly 22, and hand assembly 24 are attached to the main housing 42, they are also caused to rotate in relation to the abductor interface 44. Therefore, the shoulder flexion assembly 14 allows the prosthetic arm apparatus 10 to move along the torso simulating running motion.

Referring to FIG. 1, the shoulder flexion joint 14 is attached to the shoulder abductor 12 through the shoulder flexion assembly mount 30, shown in FIG. 5. Referring to FIG. 5, the shoulder abductor 12 is attached to a harness that is worn by the user via harness mount 26. When the shoulder abductor 12 is actuated in a positive direction, the shoulder flexion assembly mount 30 pivots away from the harness mount 26, and the user. Similarly, by actuating the shoulder abductor in a negative direction, the shoulder flexion assembly mount 30 is pivoted toward the harness mount 26 and the user. Since the shoulder flexion assembly 14, humeral rotator 16, elbow flexion assembly 18, wrist rotator 20, wrist flexion assembly 22, and hand assembly 24 are attached to shoulder abductor 12 at the flexion assembly mount 30, they are also caused to pivot with the shoulder flexion assembly mount 30.

One characteristic of the prosthetic arm apparatus described herein is that it provides the user with substantially the same movement capabilities and degrees of freedom of a human arm, including full shoulder functionality. Additionally, since each segment of the plurality of segments operates independently of each other segment of the plurality of segments, fewer segments may be used for less severe amputees. For example, a transhumeral amputee may have full shoulder functionality in the residuum, in which case the shoulder abductor 12 and shoulder flexion assembly 14 segments would be omitted from the prosthetic arm apparatus 10. The resulting prosthetic arm apparatus 10 would include the humeral rotator 16, the elbow flexion assembly 18, the wrist rotator 20, the wrist flexion assembly 22, and the hand assembly 24, wherein the humeral rotator 16 would be attached to the prosthetic harness. A further advantage of the present invention is the use of non-backdriving clutches to preclude movement of the segments due to forces exerted on the prosthetic arm apparatus 10 when not in motion. This saves power because power to the prosthetic arm apparatus 10 is turned off whenever the arm is not in motion.

An additional characteristic of the apparatus is that the hand assembly includes independently moving fingers and is capable of completing fine tasks such as pinching, grasping non-uniform objects, and lifting small objects off flat surfaces. Also, the tactile feedback sensor provides the user with feedback, during use of the prosthetic arm apparatus, such as the force of a grip. The apparatus also includes silicon covering on the finger structures, providing, amongst other things, grip for grasping objects. The rigid fingernail 304 provides a backstop for the silicon finger cover to enhance gripping capability. The rigid fingernail 304 also allows the user to lift small objects from a surface with the prosthetic arm apparatus 10.

Although the invention has been described in the context of a prosthetic arm, an apparatus according to the elements of this invention could be used in other robotic tools, such as those used in manufacturing.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. A prosthetic arm apparatus comprising:
   a plurality of interconnected segments arranged adjacent to one another from a first segment to a final segment, each segment of the plurality of interconnected segments having:
   an input interface;
   an output interface; and
   at least one actuator disposed within the segment between the input interface and the output interface, the at least one actuator driving the output interface through a drive system to cause relative movement in at least one degree of freedom between the input interface and the output interface when actuated such that each segment of the plurality of segments operates independently of each of the other segments of the plurality of interconnected segments;
   wherein one segment of the plurality of segments includes a non-backdriving clutch disposed in the drive system between the at least one actuator and the output interface, the non-backdriving clutch comprising:
   an output hex connected to the output interface of the one segment;

an input cage connected to the at least one actuator;

a clutch race constraining the input cage and the output hex; and a plurality of roller bearings disposed within the clutch race around a periphery of the output hex at an interface between the output hex and the input cage; and wherein the non-backdriving clutch transfers power from the at least one actuator to the output interface of the one segment when the actuator is actuated to generate movement of the output interface in either of two opposing directions and prevents backward transfer of power from the output interface to the at least one actuator of the one segment in both of the two opposing directions by an engagement of the output hex against the roller bearings and clutch race.

2. The prosthetic arm apparatus according to claim 1, wherein the first segment of the plurality of segments includes an interface for attaching the prosthetic arm apparatus to a harness mount for securing the prosthetic arm apparatus to a user.

3. The prosthetic arm apparatus according to claim 1, wherein each segment of the plurality of segments may be actuated independent of the other segments.

4. The prosthetic arm apparatus according to claim 1, wherein one segment of the plurality of segments includes a compliance assembly that precludes an impact force from being transmitted to the rest of the plurality of segments.

5. The prosthetic arm apparatus according to claim 1, wherein one segment of the plurality of segments includes a harmonic drive.

6. The prosthetic arm apparatus according to claim 1, wherein one of the segments of the plurality of segments includes a position-measuring device.

7. The prosthetic arm apparatus according to claim 6, wherein the position-measuring device is a potentiometer.

8. The prosthetic arm apparatus according to claim 1, wherein at least one segment of the plurality of segments houses electronic controllers for the plurality of segments.

9. The prosthetic arm apparatus according to claim 1, wherein the final segment of the plurality of segments is a hand assembly having a thumb structure, an index finger structure and a middle, ring, and pinky structure that are driven independently from each other.

10. A prosthetic arm apparatus comprising:

a plurality of interconnected segments arranged adjacent to one another from a first segment to a final segment, each segment of the plurality of interconnected segments having:

an input interface;

an output interface; and at least one actuator disposed within the segment between the input interface and the output interface, the at least one actuator driving the output interface through a drive system to cause relative movement in at least one degree of freedom between the input interface and the output interface when actuated such that each segment of the plurality of segments operates independently of each of the other segments of the plurality of interconnected segments;

wherein one segment of the plurality of segments includes a non-backdriving clutch disposed in the drive system between the at least one actuator and the output interface, the non-backdriving clutch comprising:

an output hex connected to the output interface of the one segment;

an input cage connected to the at least one actuator;

a clutch race constraining the input cage and the output hex; and a plurality of roller bearings disposed within the clutch race around a periphery of the output hex at an interface between the output hex and the input cage;

wherein the non-backdriving clutch transfers power from the at least one actuator to the output interface of the one segment when the actuator is actuated to generate movement of the output interface in either of two opposing directions and prevents backward transfer of power from the output interface to the at least one actuator of the one segment in both of the two opposing directions by an engagement of the output hex against the roller bearings and clutch race;

wherein the at least one degree of freedom of movement of each segment of the plurality of segments provides the prosthetic arm apparatus with a movement capability in a degree of freedom that correspond to a degree of freedom of movement of a human arm.

11. The prosthetic arm apparatus according to claim 10, wherein the first segment of the plurality of segments includes an interface for attaching the prosthetic arm apparatus to a harness mount for securing the prosthetic arm apparatus to a user.

12. The prosthetic arm apparatus according to claim 10, wherein each segment of the plurality of segments may be actuated independent of the other segments.

13. The prosthetic arm apparatus according to claim 10, wherein one segment of the plurality of segments includes a compliance assembly that precludes an impact force from being transmitted to the rest of the plurality of segments.

14. The prosthetic arm apparatus according to claim 10, wherein one segment of the plurality of segments includes a harmonic drive.

15. The prosthetic arm apparatus according to claim 10, wherein one of the segments of the plurality of segments includes a position-measuring device.

16. The prosthetic arm apparatus according to claim 15, wherein the position-measuring device is a potentiometer.

17. The prosthetic arm apparatus according to claim 10, wherein at least one segment of the plurality of segments houses electronic controllers for the plurality of segments.

18. The prosthetic arm apparatus according to claim 10, wherein the final segment of the plurality of segments is a hand assembly having a thumb structure, an index finger structure and a middle, ring, and pinky structure that are driven independently from each other.

* * * * *